(12) United States Patent
Takenaka et al.

(10) Patent No.: US 10,344,042 B2
(45) Date of Patent: Jul. 9, 2019

(54) PRODUCTION METHOD FOR 2-FLUORO-4-BORONO-L-PHENYLALANINE, AND PRECURSOR OF 2-FLUORO-4-BORONO-L-PHENYLALANINE

(71) Applicants: Stella Pharma Corporation, Osaka-shi, Osaka (JP); Osaka Prefecture University Public Corporation, Sakai-shi, Osaka (JP)

(72) Inventors: Hiroshi Takenaka, Osaka (JP); Yoichiro Ohta, Osaka (JP); Yusuke Taguchi, Osaka (JP); Sayuri Ueda, Osaka (JP); Yuko Ishino, Osaka (JP); Tomohiro Yoshikawa, Osaka (JP); Hideki Nakashima, Osaka (JP); Kohki Uehara, Osaka (JP); Mitsunori Kirihata, Sakai (JP)

(73) Assignees: Stella Pharma Corporation, Osaka (JP); Osaka Prefecture University Public Corporation, Osaka (JP)

( * ) Notice: Subject to any disclaimer, the term of this patent is extended or adjusted under 35 U.S.C. 154(b) by 0 days.

(21) Appl. No.: 15/625,909

(22) Filed: Jun. 16, 2017

(65) Prior Publication Data
US 2017/0283441 A1    Oct. 5, 2017

Related U.S. Application Data

(62) Division of application No. 15/105,401, filed as application No. PCT/JP2014/083243 on Dec. 16, 2014, now Pat. No. 10,005,794.

(30) Foreign Application Priority Data

Dec. 17, 2013    (JP) .................................. 2013-260451

(51) Int. Cl.
*C07F 5/02*        (2006.01)
*C07C 271/22*    (2006.01)
(Continued)

(52) U.S. Cl.
CPC .......... *C07F 5/027* (2013.01); *C07C 229/36* (2013.01); *C07C 251/24* (2013.01); *C07C 271/22* (2013.01); *Y02P 20/55* (2015.11)

(58) Field of Classification Search
CPC ... C07C 229/36; C07C 251/24; C07C 271/22; C07F 5/027; Y02P 20/55
See application file for complete search history.

(56) References Cited

U.S. PATENT DOCUMENTS 6,140,100 A    10/2000    Smith
9,409,926 B2 *    8/2016    Takenaka .................. C07F 5/04
(Continued)

FOREIGN PATENT DOCUMENTS

CN        1330077 A      1/2002
CN        101815534 A    8/2010
(Continued)

OTHER PUBLICATIONS

Lindholm (Cross-coupling reactions of organoborons with organic halides, thesis, published 2011, p. 1-107) (Year: 2011).*
(Continued)

*Primary Examiner* — Jafar F Parsa
*Assistant Examiner* — Blaine G Doletski
(74) *Attorney, Agent, or Firm* — Knobbe, Martens, Olson & Bear, LLP

(57) ABSTRACT

The present invention involves preparing compounds represented by the following formula:

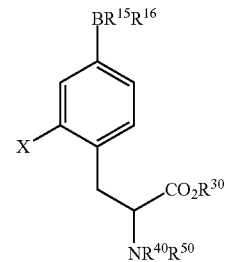

from a compound of the following formula:

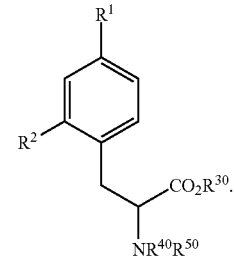

In these formulae: $R^1$ represents a Br group, an iodine group, a Cl group, an $NO_2$ group, or an $NH_2$ group; $R^2$ represents a halogen group, an $NO_2$ group, an $NH_2$ group, $Sn(R^6)_3$, $N=N-NR^7R^8$, $OSO_2R^9$, N $R^{10}R^{11}$, phenyliodonium, a heterocyclic group iodine, boric acid, or a borate ester; $R^{30}$ represents a protective group $PG^1$; $R^{40}$ or $R^{50}$ represent hydrogen, a protective group $PG^2$, or $C_6H_5(C_6H_5)C=N$, in which $NR^{40}R^{50}$ are together.

12 Claims, No Drawings

(51) Int. Cl.
*C07C 229/36* (2006.01)
*C07C 251/24* (2006.01)

(56) References Cited

U.S. PATENT DOCUMENTS

| | | | |
|---|---|---|---|
| 2009/0054308 A1* | 2/2009 | Sands | A61K 45/06 514/1.1 |
| 2009/0069592 A1 | 3/2009 | Suzuki et al. | |
| 2011/0086836 A1 | 4/2011 | Soeberdt | |
| 2015/0329564 A1 | 11/2015 | Takenaka | |

FOREIGN PATENT DOCUMENTS

| | | |
|---|---|---|
| CN | 102887913 A | 1/2013 |
| EP | 0728018 B1 | 8/1996 |
| JP | H09507834 A | 8/1997 |
| JP | 2009-532405 A | 9/2009 |
| JP | 2010-533196 A | 10/2010 |
| WO | WO 1995/13095 | 5/1995 |
| WO | WO 2007/115798 | 10/2007 |
| WO | WO2007/115798 A1 | 10/2007 |
| WO | WO 2009/009561 A1 | 1/2009 |
| WO | WO 2010/091164 | 8/2010 |
| WO | WO 2014/061508 A1 | 4/2014 |
| WO | WO 2014/140081 A1 | 9/2014 |
| WO | WO2014/140091 A1 | 9/2014 |
| WO | WO 2015/093469 A1 | 6/2015 |

OTHER PUBLICATIONS

Furstner et al. (Microwave-Assisted Synthesis of Pinacol Boronates from Aryl Chlorides Catalyzed by a Palladium/Imidazolium Salt System, Organic Letters, 4, pp. 541-543, Published 2001) (Year: 2001).*
Igor B. Sivaev et al, L-4-Boronophenylalanine (all around the one molecule, ARKIVOC 2008 (iV) 47-61).
Chinese Office Action issued in Application No. CN201480069329.1 dated Jun. 5, 2017.
Japanese Office Action issued in Application No. JP 2015-553547 dated Jun. 22, 2017.
Partial Supplementary European Search Report in Application No. PCT/JP2014083243 dated Apr. 26, 2017.
Lee, H. et al., Puromycin analogues. Effect of aryl-substituted puromycin analogues in ribosomal peptidyltransferase reaction, J. Med. Chem., 24(3), p. 304-308, 1981.
Liu, Y.-X., et al., Design, synthesis, and biological evaluation of 2-benzylpyrroles and 2-benzoylpyrroles based on structures of insecticidal chlorfenapyr and natural pyrrolomycins. Molecular Diversity, 18(3), p. 593-598, 2014.
McCord, T. J. et al., A comparative study of the rearrangement of some 6- and 7-halo-substituted 3-amino-3,4-dihydro-1-hydroxycarbostyrils in concentrated hydrohalicacids. Journal of heterocyclic Chemistry, 19(2), p. 401-406, 1982.
Pan, P.-C., et al., Synthesis of some a-substituted p-[Bis-(2-chloroethyl)-amino]-phenylalanine, Tumour Chemotherapy V, Huaxue Xuebao, 26(3), p. 131-139, 1960.
Pliska, V., et al., Side Chain lipophilicity of noncoded α-amino acids: π-values, Methods and Principles in Medicinal Chemistry, vol. 4, p. 375-386, 1996.
Samet Alexander V., et al., An Improved "One-Pot" Procedure for Synthesis of Fluorinated DL-Phenylalanines, Synthetic Communications, 32(6), p. 941-946, 2002.
Al-Darwich M.J., et al., Enantioselective synthesis of no-carrier-added (n.c.a.) (S)-4-chloro-2-[$^{18}$F] fluorophenylalanine and (S)-(α-methyl)-4-chloro-2-[$^{18}$F] fluorophenylalanine, J. Fluorine Chem., 80, p. 117-124, 1996.
Davis, Alvie L., et al., Synthesis and Antibacterial Activities of Some Chloro Analogs of 3-Amino-3,4-dihydro-1-hydroxycarbostyril, J. Med. Chem., 17(2), p. 752-755, 1975.
Jarman, Michael, et al., Synthesis of Tritum-Labeled Chlorambucil and Aniline Mustard of High Specific Activity, J. Med. Chem., 18(7), p. 194-197, 1974.
Endo, Yasuyuki, et al., Role of the hydrophobic moiety of tumor promoters, Synthesis and Activity of 9-Alkylated Berizolactams, Chem. Pharm. Bull, 44(5), p. 1138-1140, 1996.
Ishiwata, Kiichi, et al., Synthesis and Radiation Dosimetry of 4-Borono-2-[18F] Fluoro-D, L-phenylalanine; a Target Compound for PET and Boron Neutron Capture Therapy. Appl. Radiat. Isot., vol. 42, No. 4, 325-328, 1991.
McAllister, Laura A., et al., A General Strategy for the Synthesis of Cyclic N-Aryl Hydroxamic Acids via Partial Nitro Group Reduction, Journal of Organic Chemistry, 76(9), p. 3484-3497, 2011.
Vahatalo, Jyrki K., et al., Synthesis of 4-dihydroxyboryl-2-[18F]fluorophenylalanine with relatively high-specific activity. J. Labelled Compounds and Radiopharmaceuticals, 45, p. 697-704, 2002.
International Search Report for International App. No. PCT/JP2014/083243 dated Mar. 31, 2015.
Translation of International Search Report and Written Opinion issued in application No. PCT/JP2014/083243 dated Jun. 21, 2016.
Office Action received in Federal Service for Intellectual Property (ROSPATENT) RU Patent Application No. 2016128963, dated Apr. 12, 2017.
Office Action received in Chinese Patent Application No. 201480069329.1, dated Feb. 11, 2018.
CN1330077 translation (2004), pp. 1-47.
Examination Report received in Australian Patent Application No. 2014367825, dated Apr. 5, 2018.
Green (1999) in two pages.
STN 1985 (1 page published 1985).
STN 10-2011.
STN 2005 (1 page published 2005).
Office Action received in Taiwan Application No. 103144087, dated May 11, 2018.
Office Action received in Japanese Patent Application No. JP 2017-153811, dated Aug. 3, 2018. 6 pages.
Office Action received in Chinese Application No. 201480069329.1, dated Jun. 12, 2018. 14 pages.
Office Action received in Chinese Patent Application No. 201480069329.1, dated Nov. 7, 2018.
Examination Report received in Indian Patent Application No. 201647023757, dated Apr. 24, 2019.

* cited by examiner

PRODUCTION METHOD FOR 2-FLUORO-4-BORONO-L-PHENYLALANINE, AND PRECURSOR OF 2-FLUORO-4-BORONO-L-PHENYLALANINE

INCORPORATION BY REFERENCE TO ANY PRIORITY APPLICATIONS

This application is a divisional of U.S. application Ser. No. 15/105,401, filed on Jun. 16, 2016, which is the U.S. National Phase under 35 U.S.C. § 371 of International Application No. PCT/JP2014/083243, filed Dec. 15, 2014, designating the U.S., and published in Japanese as WO 2015/093469 on Jun. 25, 2015, which claims priority to Japanese Patent Application No. 2013-260451, filed Dec. 17, 2013. Any and all applications for which a foreign or domestic priority claim is identified in the Application Data Sheet as filed with the present application, including each of the aforementioned applications, is incorporated by reference herein in its entirety, and each is hereby expressly made a part of this specification

BACKGROUND OF THE INVENTION

Field of the Invention

The present invention relates to a method for producing 2-fluoro-4-borono-L-phenylalanine, 4-boronophenylalanine (fluorinated BPA)(BPA:4-Boronophenylalanine), and precursors thereof.

Description of the Related Art

At present, attention has been paid to positron emission tomography (PET) as a technique that is high in sensitivity to be excellent in quantitatively determining performance and can form images easily in light of a principle thereof. This technique has widely been used. The half value period of PET diagnostic reagents (tracers) used for diagnoses is short, and the tracers are each administrated in a fine amount so that any living body is hardly exposed to radiation based thereon. Therefore, this inspecting method is a low invasive inspecting method, thus is greatly advantageous to PET. Furthermore, PET is highly sensitive even to tumors that are not easily determined by CT (computed tomography) or MRI (magnetic resonance imaging), and tumor tissues thereof can be evaluated according to images.

$^{18}$F-labeled BPA, in which a $^{18}$F-fluorine atom is introduced into BPA, which is a boronated amino acid used as a boron reagent for BNCT (boron neutron capture therapy), was developed as a molecular probe for PET by Ishiwata in 1991 (Non-Patent Document 1). Thereafter, a PET inspection with the use of $^{18}$F-labeled BPA using the present probe has been an important technique for supporting BNCT. In other words, in clinical and research spots, a $^{18}$F-BPA PET image obtained by measuring a subject beforehand can give data on an internal accumulation distribution of BPA, the ratio of tumor tissues/normal tissues (the T/N ratio) and others. On the basis of these data, curative effects of BNCT can be beforehand assumed and then a research or therapeutic plan can be drawn up.

In Ishiwata's synthesis method, BPA is directly fluorinated to prepare 18F-labeled BPA, and 18F$^{+}$ is used as an electrophilic reagent. From deuterium (D) and neon (Ne) accelerated by a cyclotron, $^{18}$F gas is prepared, and then passed through a column filled with sodium acetate to convert the gas to $CH_3COO^{-18}F^{+}$. Thereafter, a solution of BPA in trifluoroacetic acid is bubbled by the introduction of this conversion-obtained compound into the solution. In this way, the synthesis of the target $^{18}$F-labeled BPA is attained.

As another method for synthesizing $^{18}$F-labeled BPA, Vahatalo et al. suggest a method in which such a conventional method is partially improved (Non-Paten Document 2). This method is a method of using H$^{18}$F, which can be obtained in a larger quantity, to attain the synthesis via $CH_3^{18}F$ as an intermediate of $^{18}F_2$. By causing $CH_3I$ to react with H$^{18}$F, which is obtained through the radiation of protons to $H_2^{18}O$ [through $^{18}O(p,n)^{18}F$ reaction], $CH_3^{18}F$ is once synthesized. The resultant compound $CH_3^{18}F$ is discharged to disassociate its C—F bonds to prepare $^{18}F_2$. This compound is used to synthesize $^{18}$F-labeled BPA, equivalently to Ishiwata's synthesis method.

PRIOR ART DOCUMENTS

Non-Patent Documents

Non-Patent Document 1: Appl. Radiat. Isot., 42, 325, 1991
Non-Patent Document 2: J. Label. Compd. Radiopharm., 45, 697, 2002

SUMMARY OF THE INVENTION

Problems to be Solved by the Invention

However, the $^{18}$F-labeled BPA obtained by the conventional synthesis method according to Ishiwata et al. is low in specific radioactivity and further extremely small in yield. Even by the improved method, the yield is still small although the specific radioactivity of the resultant $^{18}$F-labeled BPA species is heightened.

One of the objectives of the present invention is to provide a novel BPA derivative that can be an intermediate for synthesizing $^{18}$F-labeled BPA.

Another objective of the present invention is to provide a method for producing such a novel BPA derivative, and a method for producing fluorinated BPA, including $^{18}$F-labeled BPA, using this derivative.

Means for Solving the Problems

In order to solve the above-mentioned problems, the inventors have made eager investigations to find out a novel method for synthesizing fluorinated BPA. Thus, the present invention has been achieved.

Accordingly, the present invention relates to a compound represented by the following formula:

[Formula 1]

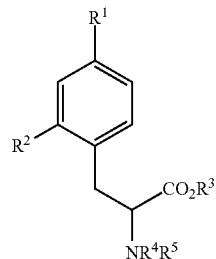

where $R^1$ represents a bromo group, an iodo group, a chloro group, a nitro group, or an amino group; $R^2$ represents a halogen group, a nitro group, an amino group, $Sn(R^6)_3$, N=N—NR⁷R⁸, $OSO_2R^9$, $NR^{10}R^{11}$, substituted or unsubstituted phenyl iodo, a substituted or unsubstituted heterocyclic iodo group, or boric acid ($B(OH)_2$) or a boric ester selected from the group consisting of pinacol, 2,2-dimethyl-1,3-propanediol, N-methyldiethanolamine, 1,8-diaminonaphthalene, N-methyliminodiacetic acid, 1,1,1-trishydroxymethylethane, and catechol (where $R^6$ represents an alkyl group having 1 to 7 carbon atoms or a benzyl group; $R^7$ and $R^8$ are the same or different, each representing hydrogen, an alkyl group having 1 to 7 carbon atoms, a halogen-substituted alkyl group having 1 to 7 carbon atoms, or an optionally substituted phenyl group, or else $R^7$ and $R^8$ are combined together with N to form a 3- to 7-membered cyclic structure; $R^9$ represents an alkyl group having 1 to 7 carbon atoms, a halogen-substituted alkyl group having 1 to 7 carbon atoms, or an optionally substituted phenyl group; $R^{10}$ and $R^{11}$ are the same or different, each representing an alkyl group having 1 to 7 carbon atoms, a halogen-substituted alkyl group having 1 to 7 carbon atoms, or an optionally substituted phenyl group, or else $R^{10}$ and $R^{11}$ are combined together with N to form a 3- to 7-membered cyclic structure); $R^3$ represents hydrogen, an ethyl group, a tert-butyl group, or a benzyl group; $R^4$ or $R^5$ independently represents hydrogen, a benzyloxycarbonyl group, or a tert-butoxycarbonyl group, or else $NR^4R^5$ are combined together to form $C_6H_5(C_6H_5)C=N$;

(except that excluded herefrom are the following cases:
1) case in which all of $R^3$, $R^4$, and $R^5$ are hydrogen, and $R^2$ is a chloro group,
2) case in which all of $R^3$, $R^4$, and $R^5$ are hydrogen; $R^2$ is a bromo group; and $R^1$ is a bromo group, a chloro group, a nitro group, or an amino group,
3) case in which all of $R^3$, $R^4$, and $R^5$ are hydrogen; $R^2$ is an iodo group; and $R^1$ is a chloro group or a nitro group,
4) case in which $R^3$ is hydrogen; $R^2$ is a chloro group; $R^1$ is a chloro group, a bromo group, or a nitro group; and one of $R^4$ and $R^5$ is hydrogen,
5) case in which $R^3$ is hydrogen; $R^2$ is a bromo group; $R^1$ is a chloro group; and one of $R^4$ and $R^5$ is hydrogen,
6) case in which $R^4$ and $R^5$ are hydrogen; $R^2$ is a chloro group; and $R^1$ is a nitro group,
7) case in which $NR^4R^5$ are combined together to form $C_6H_5(C_6H_5)C=N$, and $R^2$ is a fluoro group, and
8) case in which $R^1$ is a chloro group; $R^2$ is a fluoro group; $R^4$ and $R^5$ are hydrogen; and $R^3$ is an ethyl group).

In one embodiment, in the above-mentioned compound, $R^1$ represents a bromo group, an iodo group, a chloro group, a nitro group, or an amino group; $R^2$ represents a halogen group, a nitro group, an amino group, $Sn(R^6)_3$, N=N—NR⁷R⁸, $OSO_2R^9$, $NR^{10}R^{11}$, substituted or unsubstituted phenyl iodo, a substituted or unsubstituted heterocyclic iodo group, or boric acid ($B(OH)_2$) or a boric ester selected from the group consisting of pinacol, 2,2-dimethyl-1,3-propanediol, N-methyldiethanolamine, 1,8-diaminonaphthalene, N-methyliminodiacetic acid, 1,1,1-trishydroxymethylethane, and catechol (where $R^6$ represents an alkyl group having 1 to 7 carbon atoms or a benzyl group; $R^7$ and $R^8$ are the same or different, each representing hydrogen, an alkyl group having 1 to 7 carbon atoms, a halogen-substituted alkyl group having 1 to 7 carbon atoms, or an optionally substituted phenyl group, or else $R^7$ and $R^8$ are combined together with N to form a 3- to 7-membered cyclic structure; $R^9$ represents an alkyl group having 1 to 7 carbon atoms, a halogen-substituted alkyl group having 1 to 7 carbon atoms, or an optionally substituted phenyl group; $R^{10}$ and $R^{11}$ are the same or different, each representing an alkyl group having 1 to 7 carbon atoms, a halogen-substituted alkyl group having 1 to 7 carbon atoms, or an optionally substituted phenyl group, or else $R^{10}$ and $R^{11}$ are combined together with N to form a 3- to 7-membered cyclic structure) (here, at least one of $R^1$ and $R^2$ necessarily is a bromo group, an iodo group, or a chloro group); $R^3$ represents hydrogen, an ethyl group, a tert-butyl group, or a benzyl group; $R^4$ or $R^5$ independently represents a hydrogen, benzyloxycarbonyl group, or a tert-butoxycarbonyl group, or else $NR^4R^5$ are combined together to form $C_6H_5(C_6H_5)C=N$; (except that excluded herefrom are the following cases:
1) case in which all of $R^3$, $R^4$, and $R^5$ are hydrogen, and $R^2$ is a chloro group,
2) case in which all of $R^3$, $R^4$, and $R^5$ are hydrogen; $R^2$ is a bromo group; and $R^1$ is a bromo group, a chloro group, a nitro group, or an amino group,
3) case in which all of $R^3$, $R^4$, and $R^5$ are hydrogen; $R^2$ is an iodo group; and $R^1$ is a chloro group or a nitro group,
4) case in which $R^3$ is hydrogen; $R^2$ is a chloro group; and $R^1$ is a chloro group, a bromo group, or a nitro group,
5) case in which $R^3$ is hydrogen; $R^2$ is a bromo group; $R^1$ is a chloro group; and one of $R^4$ and $R^5$ is hydrogen,
6) case in which $R^4$ and $R^5$ are hydrogen; $R^2$ is a chloro group; and $R^1$ is a nitro group,
7) case in which $NR^4R^5$ are combined together to form $C_6H_5(C_6H_5)C=N$, and $R^2$ is a fluoro group, and
8) case in which $R^1$ is a chloro group; $R^2$ is a fluoro group; $R^4$ and $R^5$ are hydrogen; and $R^3$ is an ethyl group).

In one embodiment, in the above-mentioned compound, $R^1$ represents a bromo group, an iodo group, a chloro group, a nitro group, or an amino group; $R^2$ represents a halogen group, a nitro group, an amino group, $Sn(R^6)_3$, N=N—NR⁷R⁸, $OSO_2R^9$, $NR^{10}R^{11}$, substituted or unsubstituted phenyl iodo, a substituted or unsubstituted heterocyclic iodo group, or a boric acid ($B(OH)_2$) or a boric ester selected from the group consisting of pinacol, 2,2-dimethyl-1,3-propanediol, N-methyldiethanolamine, 1,8-diaminonaphthalene, N-methyliminodiacetic acid, 1,1,1-trishydroxymethylethane, and catechol (where $R^6$ represents an alkyl group having 1 to 7 carbon atoms or a benzyl group; $R^7$ and $R^8$ are the same or different, each representing hydrogen, an alkyl group having 1 to 7 carbon atoms, a halogen-substituted alkyl group having 1 to 7 carbon atoms, or an optionally substituted phenyl group, or else $R^7$ and $R^8$ are combined together with N to form a 3- to 7-membered cyclic structure; $R^9$ represents an alkyl group having 1 to 7 carbon atoms, a halogen-substituted alkyl group having 1 to 7 carbon atoms, or an optionally substituted phenyl group; $R^{10}$ and $R^{11}$ are the same or different, each representing an alkyl group having 1 to 7 carbon atoms, a halogen-substituted alkyl group having 1 to 7 carbon atoms, or an optionally substituted phenyl group, or else $R^{10}$ and $R^{11}$ are combined together with N to form a 3- to 7-membered cyclic structure) (here, at least one of $R^1$ and $R^2$ necessarily is a bromo group, an iodo group, or a chloro group); $R^3$ represents hydrogen, an ethyl group, a tert-butyl group, or a benzyl group; $R^4$ or $R^5$ independently represents hydrogen, a benzyloxycarbonyl group, or a tert-butoxycarbonyl group, or else $NR^4R^5$ are combined together to form $C_6H_5(C_6H_5)C=N$; (except that excluded herefrom are the following cases:
1) case in which all of $R^3$, $R^4$, and $R^5$ are hydrogen, and $R^2$ is a chloro group,
2) case in which all of $R^3$, $R^4$, and $R^5$ are hydrogen; $R^2$ is a bromo group; and $R^1$ is a bromo group, a chloro group, a nitro group, or an amino group,
3) case in which all of $R^3$, $R^4$, and $R^5$ are hydrogen; $R^2$ is an iodo group; and $R^1$ is a chloro group or a nitro group, 4) case in which $R^3$ is hydrogen; $R^2$ is a chloro group; and $R^1$ is a chloro group, a bromo group, or a nitro group,
5) case in which $R^3$ is hydrogen; $R^2$ is a bromo group; and $R^1$ is a chloro group,
6) case in which $R^4$ and $R^5$ are hydrogen; $R^2$ is a chloro group; and $R^1$ is a nitro group,
7) case in which $NR^4R^5$ are combined together to form $C_6H_5(C_6H_5)C=N$, and $R^2$ is a fluoro group, and
8) case in which $R^1$ is a chloro group; $R^2$ is a fluoro group; $R^4$ and $R^5$ are hydrogen; and $R^3$ is an ethyl group).

The present invention also relates to a method for producing a compound represented by the following formula:

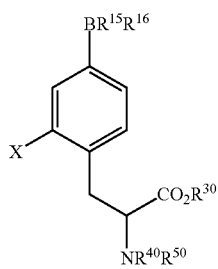

[Formula 2]

(where X represents F or $^{18}F$; $R^{30}$ represents hydrogen or a protecting group $PG^1$ for a carboxyl group; $R^{40}$ or $R^{50}$ independently represents hydrogen or a protecting group $PG^2$ for an amino group, or else $NR^{40}R^{50}$ are combined together to form $C_6H_5(C_6H_5)C=N$; and $R^{15}$ and $R^{16}$ are combined together with B (boron atom) to form a ring serving as a protecting group for B), comprising the step of using a compound represented by the following formula:

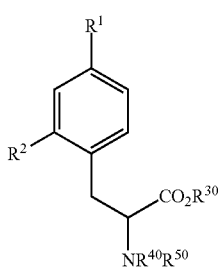

[Formula 3]

where $R^1$ represents a bromo group, an iodo group, a chloro group, a nitro group, or an amino group; $R^2$ represents a halogen group, a nitro group, an amino group, $Sn(R^6)_3$, $N=N-NR^7R^8$, $OSO_2R^9$, $NR^{10}R^{11}$, substituted or unsubstituted phenyl iodo, a substituted or unsubstituted heterocyclic iodo group, or boric acid or a boric ester (where $R^6$ represents an alkyl group having 1 to 7 carbon atoms or a benzyl group; $R^7$ and $R^8$ are the same or different, each representing hydrogen, an alkyl group having 1 to 7 carbon atoms, a halogen-substituted alkyl group having 1 to 7 carbon atoms, or an optionally substituted phenyl group, or else $R^7$ and $R^8$ are combined together with N to form a 3- to 7-membered cyclic structure; $R^9$ represents an alkyl group having 1 to 7 carbon atoms, a halogen-substituted alkyl group having 1 to 7 carbon atoms, or an optionally substituted phenyl group; $R^{10}$ and $R^{11}$ are the same or different, each representing an alkyl group having 1 to 7 carbon atoms, a halogen-substituted alkyl group having 1 to 7 carbon atoms, or an optionally substituted phenyl group, or else $R^{10}$ and $R^{11}$ are combined together with N to form a 3- to 7-membered cyclic structure); and $R^{30}$, $R^{40}$, and $R^{50}$ have the same meaning as described above.

The present invention also relates to a method for producing $^{18}F$-labeled BPA, comprising the step of using a compound represented by the following formula:

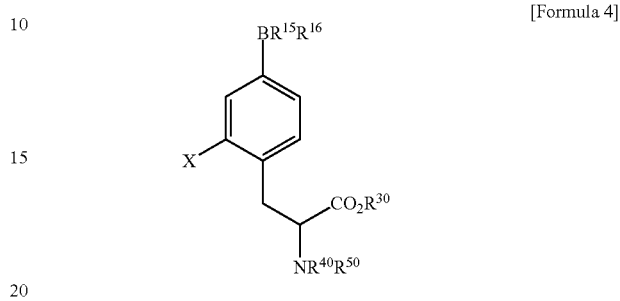

[Formula 4]

(where X represents F or $^{18}F$; $R^{30}$, $R^{40}$, and $R^{50}$ have the same meaning as described above; and $R^{15}$ and $R^{16}$ are combined together with B (boron atom) to form a ring serving as a protecting group for B).

EFFECT OF THE INVENTION

The novel compound and the production method of the present invention are favorably usable, particularly, for producing $^{18}F$-labeled BPA.

MODE FOR CARRYING OUT THE INVENTION

The existing methods for synthesizing $^{18}F$-labeled BPA are methods for fluorinating BPA directly, and are attained, in particular, by conducting an electrophilic reaction by use of $^{18}F$ as an electrophilic reagent. The inventors have paid attention to the following: in the step of preparing $^{18}F_2$ gas in a cyclotron, the step of using $F^+$ from the resultant $^{18}F_2$ gas, and some other steps in such an existing synthesis route, problems are caused, respectively; and further, $^{18}F$-labeled BPA obtained finally has a lowered specific radioactivity by the generation of a reaction product from intermingled $^{19}F_2$ molecules or by some other causes, and the quantity of $^{18}F$-labeled BPA usable for PET diagnosis according to a single synthesis is a quantity for only several persons. A novel method of the present invention for synthesizing $^{18}F$-labeled BPA is entirely different from the conventional methods, and is a synthesis method in which $^{18}F$ anions are usable. This method imposes little load on the apparatus, and makes it possible to synthesize $^{18}F$-labeled BPA to give a yield larger than the respective yields according to the conventional synthesis methods.

In the present invention, first, a novel method for producing fluorinated BPA, in particular, a method for producing $^{18}F$-labeled BPA, is found out. Further, in such novel method for producing $^{18}F$-labeled BPA, several novel intermediate compounds are obtained. By this novel method for producing $^{18}F$-labeled BPA, $^{18}F$-labeled BPA can be obtained at a high yield in a simple and convenient manner.

In the present invention, here, the wording "fluorinated BPA" denotes:

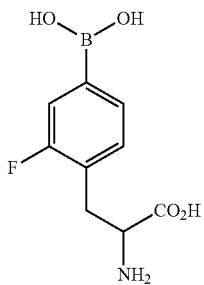
[Formula 5]

or is used as a term including the following $^{18}$F-labeled BPA. Here, the $^{18}$F-labeled BPA denotes:

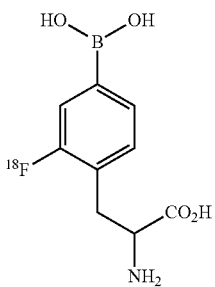
[Formula 6]

In the present invention, a novel intermediate compound that finally leads to synthesis of these fluorinated BPA compounds is provided.

In the present invention, the novel intermediate compound has the same meaning as a compound represented by the following formula:

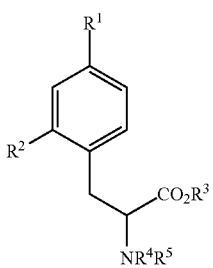
[Formula 7]

where $R^1$ represents a bromo group, an iodo group, a chloro group, a nitro group, or an amino group; $R^2$ represents a halogen group, a nitro group, an amino group, $Sn(R^6)_3$, $N=N-NR^7R^8$, $OSO_2R^9$, $NR^{10}R^{11}$, substituted or unsubstituted phenyl iodo, a substituted or unsubstituted heterocyclic iodo group, or boric acid $(B(OH)_2)$, or a boric ester selected from the group consisting of pinacol, 2,2-dimethyl-1,3-propanediol, N-methyldiethanolamine, 1,8-diaminonaphthalene, N-methyliminodiacetic acid, 1,1,1-trishydroxymethylethane, and catechol (where $R^6$ represents an alkyl group having 1 to 7 carbon atoms or a benzyl group; $R^7$ and $R^8$ are the same or different, each representing hydrogen, an alkyl group having 1 to 7 carbon atoms, a halogen-substituted alkyl group having 1 to 7 carbon atoms, or an optionally substituted phenyl group, or else $R^7$ and $R^8$ are combined together with N to form a 3- to 7-membered cyclic structure; $R^9$ represents an alkyl group having 1 to 7 carbon atoms, a halogen-substituted alkyl group having 1 to 7 carbon atoms, or an optionally substituted phenyl group; $R^{10}$ and $R^{11}$ are the same or different, each representing an alkyl group having 1 to 7 carbon atoms, a halogen-substituted alkyl group having 1 to 7 carbon atoms, or an optionally substituted phenyl group, or else $R^{10}$ and $R^{11}$ are combined together with N to form a 3- to 7-membered cyclic structure); $R^3$ represents hydrogen, an ethyl group, a tert-butyl group, or a benzyl group; $R^4$ or $R^5$ independently represents hydrogen, a benzyloxycarbonyl group, or a tert-butoxycarbonyl group, or else $NR^4R^5$ are combined together to form $C_6H_5(C_6H_5)C=N$;
(except that excluded herefrom are the following cases:
1) case in which all of $R^3$, $R^4$, and $R^5$ are hydrogen, and $R^2$ is a chloro group,
2) case in which all of $R^3$, $R^4$, and $R^5$ are hydrogen; $R^2$ is a bromo group; and $R^1$ is a bromo group, a chloro group, a nitro group, or an amino group,
3) case in which all of $R^3$, $R^4$, and $R^5$ are hydrogen; $R^2$ is an iodo group; and $R^1$ is a chloro group or a nitro group,
4) case in which $R^3$ is hydrogen; $R^2$ is a chloro group; $R^1$ is a chloro group, a bromo group, or a nitro group; and one of $R^4$ and $R^5$ is hydrogen,
5) case in which $R^3$ is hydrogen; $R^2$ is a bromo group; $R^1$ is a chloro group; and one of $R^4$ and $R^5$ is hydrogen,
6) case in which $R^4$ and $R^5$ are hydrogen; $R^2$ is a chloro group; and $R^1$ is a nitro group,
7) case in which $NR^4R^5$ are combined together to form $C_6H_5(C_6H_5)C=N$, and $R^2$ is a fluoro group, and
8) case in which $R^1$ is a chloro group; $R^2$ is a fluoro group; $R^4$ and $R^5$ are hydrogen; and $R^3$ is an ethyl group).

Though not particularly limited, it is preferable further that $R^1$ represents a bromo group, an iodo group, a chloro group, a nitro group, or an amino group; $R^2$ represents a halogen group, a nitro group, an amino group, $Sn(R^6)_3$, $N=N-NR^7R^8$, $OSO_2R^9$, $NR^{10}R^{11}$, substituted or unsubstituted phenyl iodo, a substituted or unsubstituted heterocyclic iodo group, or boric acid $(B(OH)_2)$ or a boric ester selected from the group consisting of pinacol, 2,2-dimethyl-1,3-propanediol, N-methyldiethanolamine, 1,8-diaminonaphthalene, N-methyliminodiacetic acid, 1,1,1-trishydroxymethylethane, and catechol (where $R^6$ represents an alkyl group having 1 to 7 carbon atoms or a benzyl group; $R^7$ and $R^8$ are the same or different, each representing hydrogen, an alkyl group having 1 to 7 carbon atoms, a halogen-substituted alkyl group having 1 to 7 carbon atoms, or an optionally substituted phenyl group, or else $R^7$ and $R^8$ are combined together with N to form a 3- to 7-membered cyclic structure; $R^9$ represents an alkyl group having 1 to 7 carbon atoms, a halogen-substituted alkyl group having 1 to 7 carbon atoms, or an optionally substituted phenyl group; $R^{10}$ and $R^{11}$ are the same or different, each representing an alkyl group having 1 to 7 carbon atoms, halogen-substituted alkyl group having 1 to 7 carbon atoms, or an optionally substituted phenyl group, or else $R^{10}$ and $R^{11}$ are combined together with N to form a 3- to 7-membered cyclic structure) (here, at least one of $R^1$ and $R^2$ necessarily is a bromo group, an iodo group, or a chloro group); $R^3$ represents hydrogen, an ethyl group, a tert-butyl group, or a benzyl group; $R^4$ or $R^5$ independently represents hydrogen, a benzyloxycarbonyl group, or a tert-butoxycarbonyl group, or else $NR^4R^5$ are combined together to form $C_6H_5(C_6H_5)C=N$; (except that excluded herefrom are the following cases:
1) case in which all of $R^3$, $R^4$, and $R^5$ are hydrogen, and $R^2$ is a chloro group, 2) case in which all of $R^3$, $R^4$, and $R^5$ are hydrogen; $R^2$ is a bromo group; and $R^1$ is a bromo group, a chloro group, a nitro group, or an amino group,
3) case in which all of $R^3$, $R^4$, and $R^5$ are hydrogen; $R^2$ is an iodo group; and $R^1$ is a chloro group or a nitro group,
4) case in which $R^3$ is hydrogen; $R^2$ is a chloro group; and $R^1$ is a chloro group, a bromo group, or a nitro group,
5) case in which $R^3$ is hydrogen; $R^2$ is a bromo group; $R^1$ is a chloro group; and one of $R^4$ and $R^5$ is hydrogen,
6) case in which $R^4$ and $R^5$ are hydrogen; $R^2$ is a chloro group; and $R^1$ is a nitro group,
7) case in which $NR^4R^5$ are combined together to form $C_6H_5(C_6H_5)C=N$, and $R^2$ is a fluoro group, and
8) case in which $R^1$ is a chloro group; $R^2$ is a fluoro group; $R^4$ and $R^5$ are hydrogen; and $R^3$ is an ethyl group).

Further, in another embodiment, it is preferable that $R^1$ represents a bromo group, an iodo group, a chloro group, a nitro group, or an amino group; $R^2$ represents a halogen group, a nitro group, an amino group, $Sn(R^6)_3$, $N=N-NR^7R^8$, $OSO_2R^9$, $NR^{10}R^{11}$, substituted or unsubstituted phenyl iodo, a substituted or unsubstituted heterocyclic iodo group, or boric acid $(B(OH)_2)$ or a boric ester selected from the group consisting of pinacol, 2,2-dimethyl-1,3-propanediol, N-methyldiethanolamine, 1,8-diaminonaphthalene, N-methyliminodiacetic acid, 1,1,1-trishydroxymethylethane, and catechol (where $R^6$ represents an alkyl group having 1 to 7 carbon atoms or a benzyl group; $R^7$ and $R^8$ are the same or different, each representing hydrogen, an alkyl group having 1 to 7 carbon atoms, a halogen-substituted alkyl group having 1 to 7 carbon atoms, or an optionally substituted phenyl group, or else $R^7$ and $R^8$ are combined together with N to form a 3- to 7-membered cyclic structure; $R^9$ represents an alkyl group having 1 to 7 carbon atoms, a halogen-substituted alkyl group having 1 to 7 carbon atoms, or an optionally substituted phenyl group; $R^{10}$ and $R^{11}$ are the same or different, each representing an alkyl group having 1 to 7 carbon atoms, a halogen-substituted alkyl group having 1 to 7 carbon atoms, or an optionally substituted phenyl group, or else $R^{10}$ and $R^{11}$ are combined together with N to form a 3- to 7-membered cyclic structure) (here, at least one of $R^1$ and $R^2$ necessarily is a bromo group, an iodo group, or a chloro group); $R^3$ represents hydrogen, an ethyl group, a tert-butyl group, or a benzyl group; $R^4$ or $R^5$ independently represents hydrogen, a benzyloxycarbonyl group, or a tert-butoxycarbonyl group, or else $NR^4R^5$ are combined together to form $C_6H_5(C_6H_5)C=N$; (except that excluded herefrom are the following cases:
1) case in which all of $R^3$, $R^4$, and $R^5$ are hydrogen, and $R^2$ is a chloro group,
2) case in which all of $R^3$, $R^4$, and $R^5$ are hydrogen; $R^2$ is a bromo group; and $R^1$ is a bromo group, a chloro group, a nitro group, or an amino group,
3) case in which all of $R^3$, $R^4$, and $R^5$ are hydrogen; $R^2$ is an iodo group; and $R^1$ is a chloro group or a nitro group,
4) case in which $R^3$ is hydrogen; $R^2$ is a chloro group; and $R^1$ is a chloro group, a bromo group, or a nitro group,
5) case in which $R^3$ is hydrogen; $R^2$ is a bromo group; and $R^1$ is a chloro group,
6) case in which $R^4$ and $R^5$ are hydrogen; $R^2$ is a chloro group; and $R^1$ is a nitro group,
7) case in which $NR^4R^5$ are combined together to form $C_6H_5(C_6H_5)C=N$, and $R^2$ is a fluoro group, and
8) case in which $R^1$ is a chloro group; $R^2$ is a fluoro group; $R^4$ and $R^5$ are hydrogen; and $R^3$ is an ethyl group).

Further, in another embodiment, it is preferable that $R^1$ represents a bromo group, an iodo group, a chloro group, a nitro group, or an amino group; $R^2$ represents a halogen group, a nitro group, an amino group, $Sn(R^6)_3$, $N=N-NR^7R^8$, $OSO_2R^9$, $NR^{10}R^{11}$, $I^+R^{13}$, $(R^{14-})I^+R^{13}$, or boric acid or a boric ester selected from the group consisting of pinacol, 2,2-dimethyl-1,3-propanediol, N-methyldiethanolamine, 1,8-diaminonaphthalene, N-methyliminodiacetic acid, 1,1,1-trishydroxymethylethane, and catechol (where $R^6$ represents methyl or n-butyl; $R^7$ and $R^8$ are the same or different, each representing hydrogen, methyl, ethyl, propyl, butyl, heptyl, trifluoromethyl, or an optionally substituted phenyl group, or else $R^7$ and $R^8$ are combined together with N to form aziridine, azetidine, pyrrolidine, or piperidine; $R^9$ represents methyl, ethyl, propyl, butyl, heptyl, trifluoromethyl, or an optionally substituted phenyl group; $R^{10}$ and $R^{11}$ are the same or different, each representing methyl, ethyl, propyl, butyl, heptyl, trifluoromethyl, or an optionally substituted phenyl group, or else $R^{10}$ and $R^{11}$ are combined together with N to form aziridine, azetidine, pyrrolidine, or piperidine; $R^{13}$ represents a $C_{1-6}$-alkyl-substituted phenyl group, a $C_{1-6}$-alkoxy-substituted phenyl group, or a phenyl group, or else represents a 5- to 7-membered heterocyclic group having one or more of N, S, and O atoms; and $R^{14}$ represents halogen, a tetrafluoroborate group, a nitrate group, a triflate group, a sulfonyloxy group, a toluenesulfonyloxy group, or a perchlorate group) (here, at least one of $R^1$ and $R^2$ necessarily is a bromo group, an iodo group, or a chloro group); $R^3$ represents hydrogen, an ethyl group, a tert-butyl group, or a benzyl group; $R^4$ represents hydrogen; $R^5$ represents hydrogen, a benzyloxycarbonyl group, or a tert-butoxycarbonyl group, or else $NR^4R^5$ are combined together to form $C_6H_5(C_6H_5)C=N$; (except that excluded herefrom are the following cases:
1) case in which all of $R^3$, $R^4$, and $R^5$ are hydrogen, and $R^2$ is a chloro group,
2) case in which all of $R^3$, $R^4$, and $R^5$ are hydrogen; $R^2$ is a bromo group; and $R^1$ is a bromo group, a chloro group, a nitro group, or an amino group,
3) case in which all of $R^3$, $R^4$, and $R^5$ are hydrogen; $R^2$ is an iodo group; and $R^1$ is a chloro group or a nitro group,
4) case in which $R^3$ is hydrogen; $R^2$ is a chloro group; and $R^1$ is a chloro group, a bromo group, or a nitro group (here, one of $R^4$ and $R^5$ can be hydrogen; however, a case in which neither of $R^4$ nor $R^5$ is hydrogen is also included),
5) case in which $R^3$ is hydrogen; $R^2$ is a bromo group; and $R^1$ is a chloro group (here, one of $R^4$ and $R^5$ can be hydrogen; however, a case in which neither of $R^4$ nor $R^5$ is hydrogen is also included),
6) case in which $R^4$ and $R^5$ are hydrogen; $R^2$ is a chloro group; and $R^1$ is a nitro group,
7) case in which $NR^4R^5$ are combined together to form $C_6H_5(C_6H_5)C=N$, and $R^2$ is a fluoro group, and
8) case in which $R^1$ is a chloro group; $R^2$ is a fluoro group; $R^4$ and $R^5$ are hydrogen; and $R^3$ is an ethyl group).

The novel intermediate compound of the present invention is particularly preferably the compound described above, wherein $R^1$ represents a bromo group, an iodo group, or a chloro group, and $R^2$ represents $Sn(R^6)_3$, $N=N-NR^7R^8$, $OSO_2R^9$, $NR^{10}R^{11}$, $I^+R^{13}$, $(R^{14-})I^+R^{13}$, or boric acid or one of pinacol, 2,2-dimethyl-1,3-propanediol, N-methyldiethanolamine, 1,8-diaminonaphthalene, N-methyliminodiacetic acid, 1,1,1-trishydroxymethylethane, and catechol.

The novel intermediate compound of the present invention is particularly preferably the compound described above, wherein $R^2$ is an iodo group or a bromo group.

The novel compound of the present invention is particularly preferably provided, for example, as an intermediate compound for preparing PET diagnostic pharmaceuticals, although not limited thereto.

In the present invention, a compound represented by the following formula:

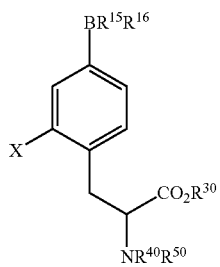

[Formula 9]

(where X represents F or $^{18}$F; $R^{30}$ represents hydrogen or a protecting group $PG^1$ for a carboxyl group; and $R^{40}$ or $R^{50}$ independently represents hydrogen or a protecting group $PG^2$ for an amino group, or else $NR^{40}R^{50}$ are combined together to form $C_6H_5(C_6H_5)C=N$; and $R^{15}$ and $R^{16}$ are combined together with B (boron atom) to form a ring serving as a protecting group for B) can be produced by using a compound represented by the following formula:

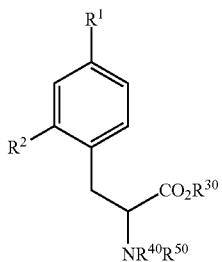

[Formula 8]

where $R^1$ represents a bromo group, an iodo group, a chloro group, a nitro group, or an amino group; $R^2$ represents a halogen group, a nitro group, an amino group, $Sn(R^6)_3$, $N=N-NR^7R^8$, $OSO_2R^9$, $NR^{10}R^{11}$, substituted or unsubstituted phenyl iodo, a substituted or unsubstituted heterocyclic iodo group, or boric acid or a boric ester (where $R^6$ represents an alkyl group having 1 to 7 carbon atoms or a benzyl group; $R^7$ and $R^8$ are the same or different, each representing hydrogen, an alkyl group having 1 to 7 carbon atoms, a halogen-substituted alkyl group having 1 to 7 carbon atoms, or an optionally substituted phenyl group, or else $R^7$ and $R^8$ are combined together with N to form a 3- to 7-membered cyclic structure; $R^9$ represents an alkyl group having 1 to 7 carbon atoms, a halogen-substituted alkyl group having 1 to 7 carbon atoms, or an optionally substituted phenyl group; $R^{10}$ and $R^{11}$ are the same or different, each representing an alkyl group having 1 to 7 carbon atoms, a halogen-substituted alkyl group having 1 to 7 carbon atoms, or an optionally substituted phenyl group, or else $R^{10}$ and $R^{11}$ are combined together with N to form a 3- to 7-membered cyclic structure) (it is preferable that at least one of $R^1$ and $R^2$ necessarily is a bromo group, an iodo group, or a chloro group); and $R^{30}$, $R^{40}$, and $R^{50}$ have the same meaning as described above. Thus obtained compound can be used to finally produce fluorinated BPA, in particular, $^{18}$F-labeled BPA.

In the present invention, $^{18}$F-labeled BPA can be produced by using a compound represented by the following formula:

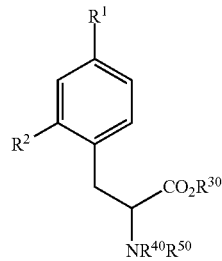

[Formula 10]

where $R^1$ represents a bromo group, an iodo group, a chloro group, a nitro group, or an amino group; $R^2$ represents a halogen group, a nitro group, an amino group, $Sn(R^6)_3$, $N=N-NR^7R^8$, $OSO_2R^9$, $NR^{10}R^{11}$, substituted or unsubstituted phenyl iodo, a substituted or unsubstituted heterocyclic iodo group, boric acid, or a boric ester (particularly preferably pinacol, 2,2-dimethyl-1,3-propanediol, N-methyldiethanolamine, 1,8-diaminonaphthalene, N-methyliminodiacetic acid, 1,1,1-trishydroxymethylethane, or catechol) (where $R^6$ represents an alkyl group having 1 to 7 carbon atoms or a benzyl group; $R^7$ and $R^8$ are the same or different, each representing hydrogen, an alkyl group having 1 to 7 carbon atoms, a halogen-substituted alkyl group having 1 to 7 carbon atoms, or an optionally substituted phenyl group, or else $R^7$ and $R^8$ are combined together with N to form a 3- to 7-membered cyclic structure; $R^9$ represents an alkyl group having 1 to 7 carbon atoms, a halogen-substituted alkyl group having 1 to 7 carbon atoms, or an optionally substituted phenyl group; $R^{10}$ and $R^{11}$ are the same or different, each representing an alkyl group having 1 to 7 carbon atoms, a halogen-substituted alkyl group having 1 to 7 carbon atoms, or an optionally substituted phenyl group, or else $R^{10}$ and $R^{11}$ are combined together with N to form a 3- to 7-membered cyclic structure) (here, at least one of $R^1$ and $R^2$ necessarily is a bromo group, an iodo group, or a chloro group); $R^{30}$ represents hydrogen or a protecting group $PG^1$ for a carboxyl group; and $R^{40}$ or $R^{50}$ independently represents hydrogen or a protecting group $PG^2$ for an amino group, or else $NR^{40}R^{50}$ are combined together to form $C_6H_5(C_6H_5)C=N$.

In the present specification, the wording "are combined together with N to form a cyclic structure having 3 to 7 atoms" denotes a saturated or unsaturated ring having carbon and nitrogen. Although not limited, examples thereof include piperidine, piperazine, pyrrolidine, pyridine, pyrimidine, pyrazine, pyrazole, and imidazole.

In the present specification, the wording heterocyclic group denotes a group having a saturated or unsaturated cyclic structure having carbon and an atom other than carbon and, in particular, thienyl group, furanyl group, pyridinyl group, piperidinyl group, piperazinyl group, and the like are preferable.

$R^{30}$ represents hydrogen or a protecting group $PG^1$ for a carboxylic acid. Here, $PG^1$ is not particularly limited and denotes any protecting group known by those skilled in the art for a carboxylic acid. Examples thereof include protecting groups described in Greene Wuts, "Protective Groups in Organic Synthesis", 3rd edition (a company, Wiley-Interscience in USA). Typically, the group concerned can be converted into an ester type to be protected, using ester condensation conditions or alkylation conditions. $PG^1$ is, for example, an alkyl group having 1 to 7 carbon atoms or an aromatic group such as a benzyl group. Specific examples thereof include alkyl groups such as a methyl group, an ethyl group, an n-propyl group, an iso-propyl group, an n-butyl group, an iso-butyl group, a sec-butyl group, a tert-butyl group, and an n-pentyl group, and aromatic groups such as a benzyl, p-methoxybenzyl, and p-nitrobenzyl groups. $PG^1$ is in particular preferably a tert-butyl or a benzyl group, which is not easily affected by racemization when de-protection is carried out. Also, $R^{30}$ may have the same meaning as $R^3$.

$R^{40}$ or $R^{50}$ independently represents hydrogen or a protecting group $PG^2$ for an amino group. The protecting group for an amino acid may be any protecting group known by those skilled in the art. Examples thereof include protecting groups described in Greene Wuts, "Protective Groups in Organic Synthesis", 3rd edition (the company, Wiley-Interscience in USA). Preferred examples thereof include a benzyloxycarbonyl group, an acetyl group, a trifluoroethyl-carboxy group, a tert-butyloxycarbonyl group, a fluorenyl-methyloxycarbonyl group, a trichloroethoxycarbonyl group, a trifluoroacetyl group, an allyloxycarbonyl group, a benzyl group, a propargyloxycarbonyl group, a benzoyl group, a phthaloyl group, a toluenesulfonyl group, and a nitrobenzenesulfonyl group, although the protecting group is not limited thereto. Of these examples, a benzyloxycarbonyl group and a tert-butyloxycarbonyl group are preferred, which can be subjected to de-protection in a short period of time. $R^{40}$ or $R^{50}$ may have the same meaning as $R^4$ and $R^5$, respectively.

In the present specification, when $R^{15}$ and $R^{16}$ are combined together with B (boron atom) to form a ring as a protecting group for B, $R^{15}$ and $R^{16}$ are preferably a group that forms a saturated or unsaturated 3- to 10-membered ring which may be substituted. Examples of the structure of the ring herein also include spiro-rings and condensed rings. Examples of the group that can form the ring include pinacol, 2,2-dimethyl-1,3-propanediol, N-methyldiethanolamine, 1,8-diaminonaphthalene, N-methyliminodiacetic acid, 1,1,1-trishydroxymethylethane, and catechol, although the group is not limited. In particular, pinacol is preferred.

In the present specification, the alkyl group having 1 to 7 carbon atoms is in particular preferably a methyl group, an ethyl group, an n-propyl group, an iso-propyl group, an n-butyl group, an iso-butyl group, a sec-butyl group, a tert-butyl group, or an n-pentyl group. The halogen-substituted alkyl group denotes an alkyl group having 1 to 7 carbon atoms wherein an arbitrary number of the hydrogen atoms thereof are substituted with one or more halogens. The halogen-substituted alkyl group is preferably a trifluoromethyl group, although the group is not limited. The substituted phenyl group denotes a phenyl group, or a phenyl group having, at one to three positions of the phenyl group, one or more substituents independently of each other. The substituted 3- to 10-membered ring denotes a 3- to 10-membered ring, or a 3- to 10-membered ring having, at one to three positions of the 3- to 10-membered ring, one or more substituents independently of each other. The substituted heterocyclic group denotes a heterocycle, or a heterocyclic group having, at one to three positions of the heterocycle, one or more substituents independently of each other. Examples of the substituent(s) of the phenyl group, the 3- to 10-membered ring, or the heterocycle include a $C_{1-6}$ alkyl group, a $C_{1-6}$ alkoxyl group, a hydroxyl group, an amino group, and a nitro group, although the substituent(s) is/are not limited.

In the novel method for producing $^{18}F$-labeled BPA of the present invention, for example, the following step S, step T, step U, or step V may be exemplified, although the steps are not limited thereto. Here, the protecting groups used in the following reaction formulae may be appropriately changed, so that the protecting groups are not limited to these examples.

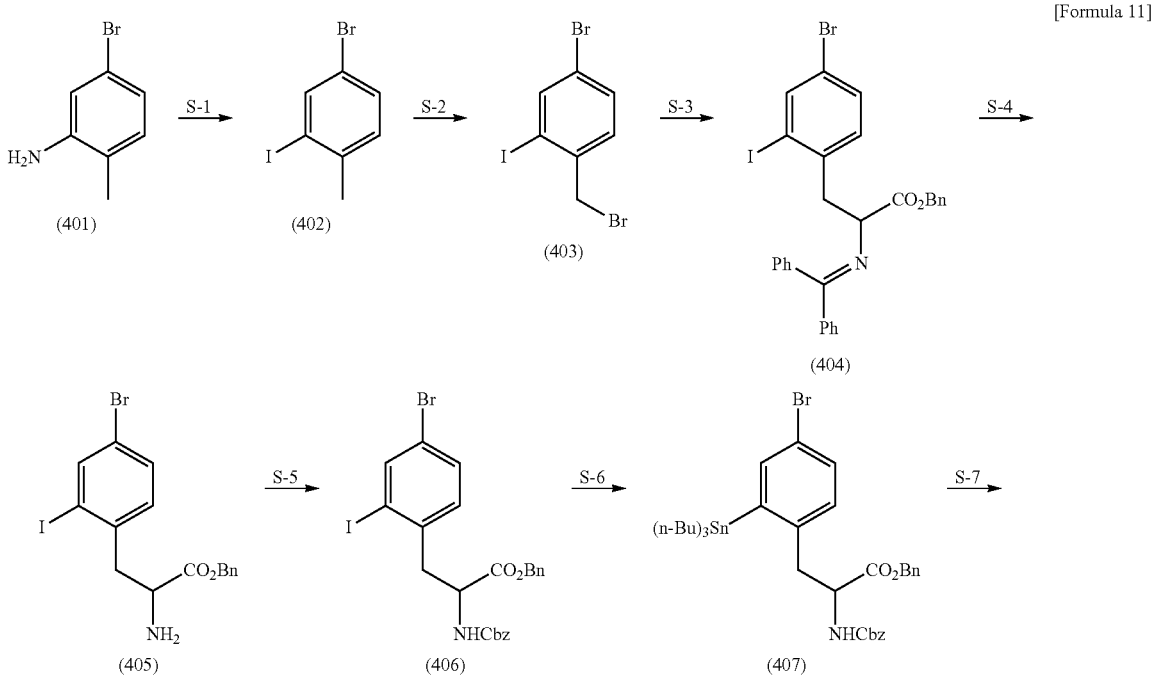

[Formula 11]

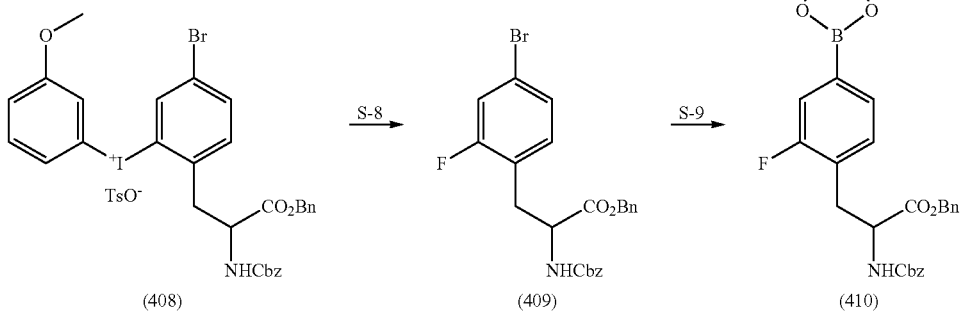
Step T
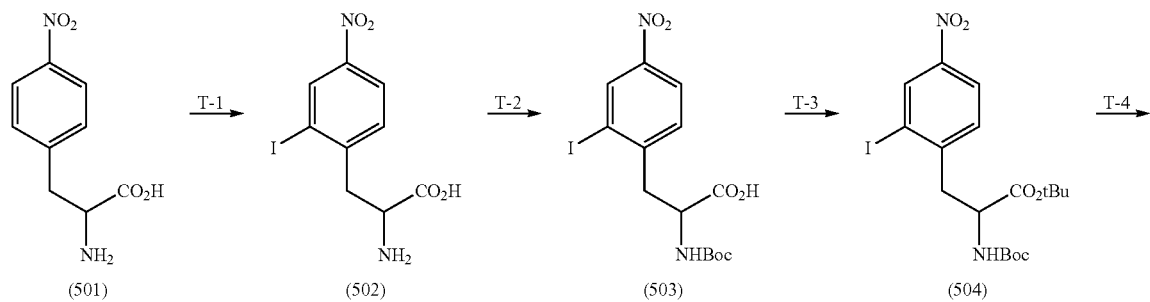
[Formula 12]
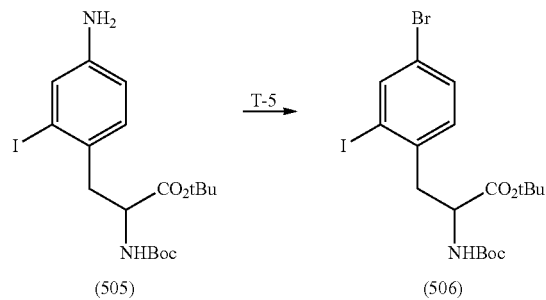
Step U
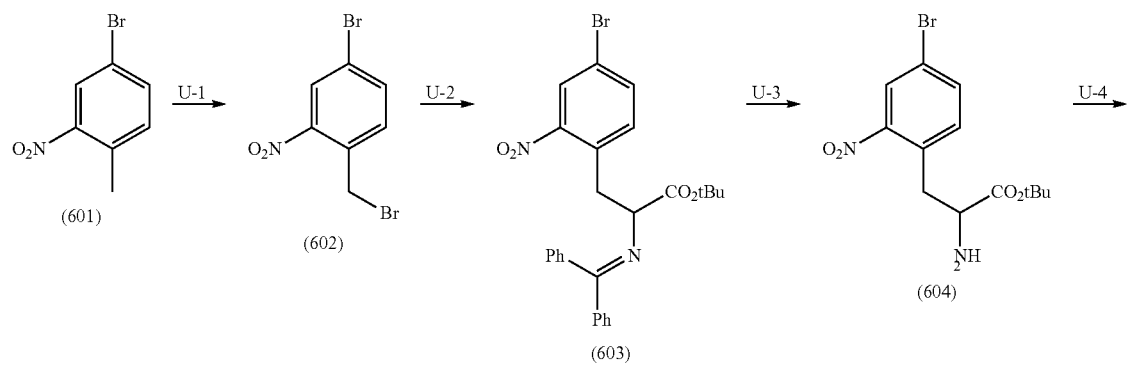
[Formula 13]

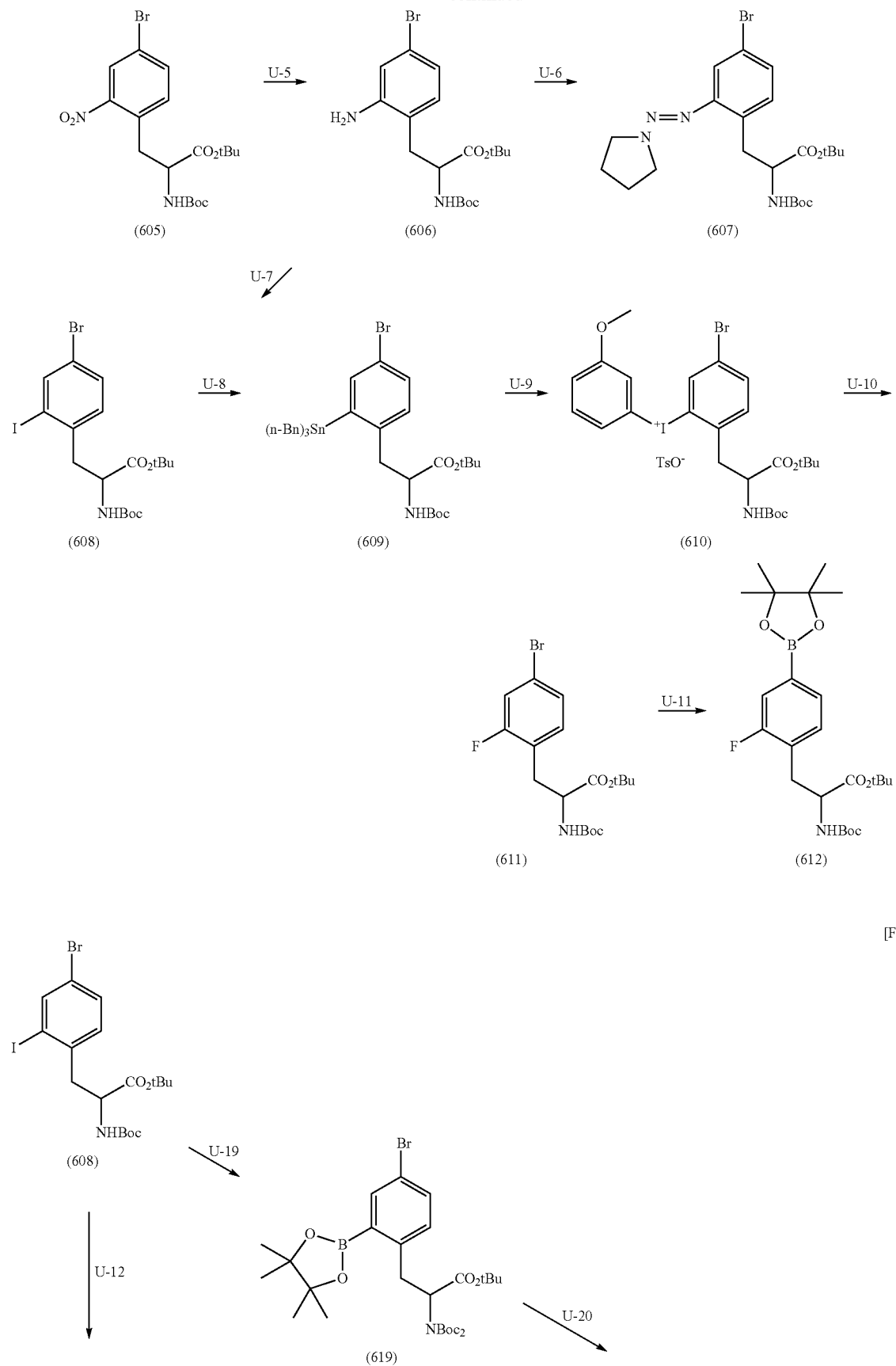

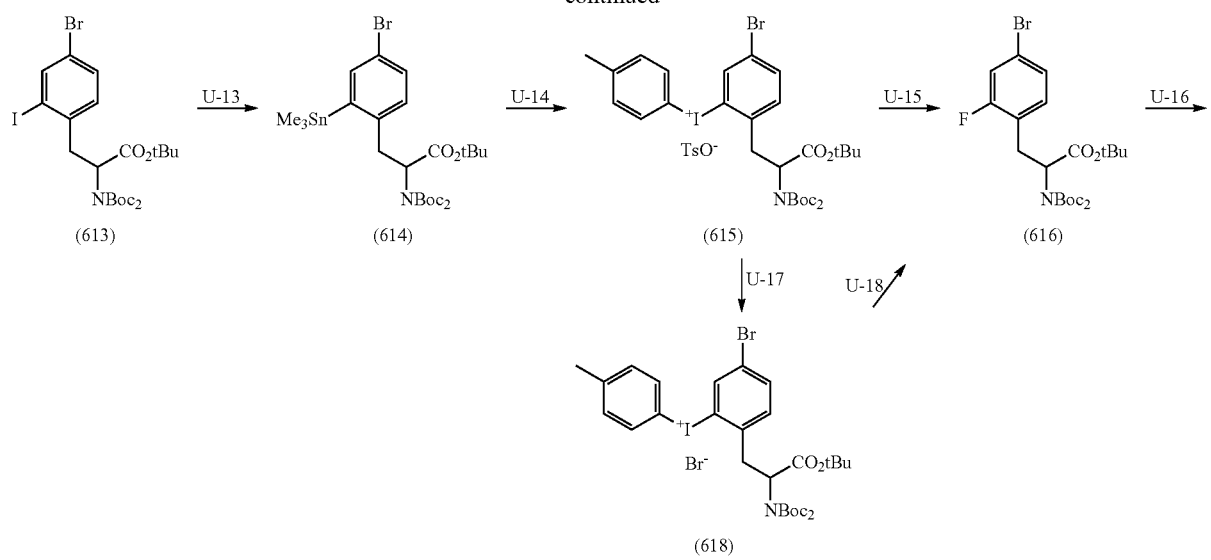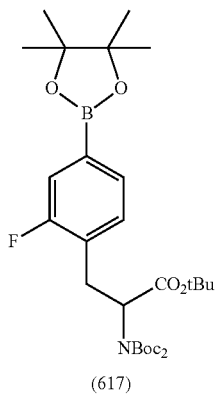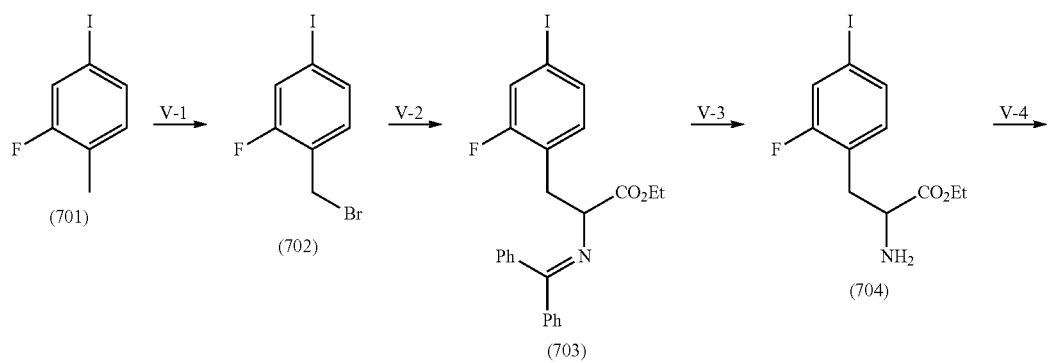

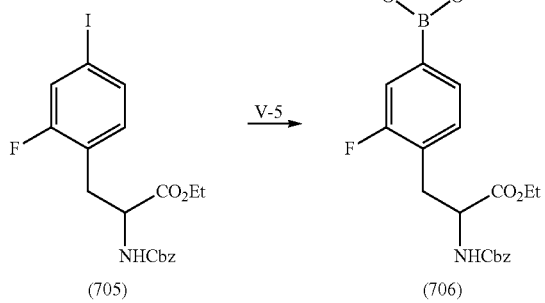

⊕ indicates text missing or illegible when filed

In the reaction in each of the steps S to V, the reaction temperature varies in accordance with the solvent, the starting materials, the reagent(s), and others, and is appropriately selected. Also, the reaction period varies in accordance with the solvent, the starting materials, the reagent(s), the reaction temperature, and others, and is appropriately selected.

In the reaction in each of the steps, the target compound of each step may be isolated from the reaction mixture by a routine procedure after the end of each reaction.

The target compound is obtained, for example, by (i) filtrating away the catalyst and other insoluble substances in accordance with the needs, (ii) adding, to the reaction mixture, water and a solvent immiscible in water (for example, ethyl acetate, chloroform, or the like) to extract the target compound, (iii) washing the organic layer with water and using a drying agent such as anhydrous magnesium sulfate to dry the resultant in accordance with the needs, and (iv) distilling off the solvent. The obtained target compound may be further purified by a known method (for example, silica gel column chromatography or the like) in accordance with the needs. Also, the target compound in each of the steps may be supplied to the next reaction without being purified.

(Step S)

In other words, Step S-1 is a step of causing a compound (401) to react with a nitrite in an acidic aqueous solution to produce a diazonium salt, so as to produce a compound (402) which is a halogen derivative. The compound (401) is known and is commercially available; however, the compound (401) may be obtained by synthesis from a commercially available compound.

The diazonium reaction reagent may be, for example, sodium nitrite, potassium nitrite, or further an alkyl nitrite such as isobutyl nitrite. Also, the iodinating reagent may be, for example, sodium iodide, potassium iodide, or iodine, which is known.

Examples of the solvent to be used include water, acetone, acetonitrile, THF, methanol, ethanol, and mixed solvents each composed of two or more kinds of these solvents. Among these, acetone is preferred, since this solvent is inactive to the diazotization reaction.

The reaction temperature is preferably from −20° C. to room temperature, more preferably from −10° C. to 5° C. The reaction period is preferably from 30 minutes to 2 hours, more preferably from 30 minutes to 1 hour.

(Step S-2)

Step S-2 is a step of causing the compound (402) to react with a halogenating reagent in the presence of a catalyst to produce a compound (403).

Examples of the halogenating reagent to be used include N-bromosuccinimide and dibromoisocyanuric acid. In the case in which a halogenating reagent other than a bromo group is used, examples of the halogenating reagent to be used include 1,3-diiodo-5,5'-dimethylhydantoin and N-iodosuccinimide. Meanwhile, the catalyst to be used is a radical polymerization agent such as a peroxide or AIBN.

The solvent to be used is not particularly limited and may be, for example, benzene, chloroform, carbon tetrachloride. Carbon tetrachloride is particularly preferred.

The reaction temperature is preferably from room temperature to 120° C., more preferably from 70° C. to 100° C.

The reaction period is preferably from 1 hour to 24 hours, more preferably from 6 hours to 18 hours.

Step S-3 is a step of causing the compound (403) to react with a phase-transfer catalyst and a modified amino acid that are generally used in Maruoka's reaction in the presence of a base to produce a compound (404) newly.

The modified amino acid to be used in Maruoka's reaction is not limited. Preferred examples thereof include a methyl ester of N-diphenylmethyleneglycine, an ethyl ester of N-diphenylmethyleneglycine, a t-butyl ester of N-diphenylmethyleneglycine N-diphenylmethyleneglycine, a t-butyl ester of 4-chlorobenzylideneglycine, and a benzyl ester ester of N-diphenylmethyleneglycine. Of these examples, particularly preferred is a t-butyl ester of N-diphenylmethyleneglycine.

The base to be used is not limited. Preferred examples thereof include lithium hydroxide, sodium hydroxide, potassium hydroxide, and further, triethylamine. In view of the reaction rate, potassium hydroxide is particularly preferred.

Preferred examples of the modified amino acid to be used in Maruoka's reaction include O-allyl-N-(9-anthracenylmethyl)cinchonidinium bromide, and (S)-(+)-4,4-dibutyll-2,6-bis(3,4,5-trifluorophenyl)-4,5-dihydro-3H-dinaphtho[7,6,1,2-CDE]azemipium bromide.

Preferred examples of the solvent to be used include toluene, dichloromethane, and chloroform. Toluene is particularly preferred in view of the environment.

The reaction temperature is preferably from −20° C. to 100° C., more preferably from −4° C. to room temperature.

The reaction period is preferably from 30 minutes to 24 hours, more preferably from 1 hour to 18 hours.

The obtained compound may be purified; however, the compound may be shifted to the next step without being purified.

(Step S-4)

Step S-4 is a step of putting the compound (404) to an acidic aqueous solution to eliminate an amino-group protector thereof. The solvent to be used therefor may be a mixed solvent of citric acid or oxalic acid in water and acetone, acetonitrile, THF, DMF, or DMSO; however, a preferable example is a mixed solvent of citric acid or oxalic acid in water and acetone, acetonitrile, or THF in view of distilling off the solvent.

Here, the reaction temperature is preferably from room temperature to 100° C., more preferably from room temperature to 80° C. The reaction period is preferably from 30 minutes to 24 hours, more preferably from 1 hour to 3 hours.

(Step S-5)

Step S-5 is a step of using a protecting reagent for the compound (405) to protect an amino group thereof under basic conditions. The protecting reagent to be used may be, for example, benzyl chloroformate, or di-t-butyl dicarbonate, although the reagent is not limited to the exemplified compounds.

Preferred examples of the base to be used include lithium hydroxide, sodium hydroxide, potassium hydroxide, sodium carbonate, potassium carbonate, and further, triethylamine, although the base is not limited thereto. In particular, sodium carbonate and potassium carbonate are preferred, which are mild.

The solvent to be used is preferably an amphipathic solvent. In particular, examples thereof include acetone, acetonitrile, THF, DMF, and DMSO. The solvent is preferably acetone, acetonitrile, or THF in view of distilling off the solvent.

The reaction temperature is preferably from −20° C. to 100° C., more preferably from −4° C. to room temperature. The reaction period is preferably from 30 minutes to 24 hours, more preferably from 3 hours to 18 hours.

(Step S-6)

Step S-6 is a step of producing, from the compound, a trialkyltin compound by a Suzuki-Miyaura coupling reaction. The reaction reagent to be used is benzyltin, and the catalyst to be used may be a palladium catalyst that is generally used in Suzuki-Miyaura coupling reaction, examples thereof including a palladium chloride cinnamyl complex, palladium acetate, trisdibenzylideneacetonedipalladium, and tetrakistriphenylphenylphosphinopalladium, although the catalyst is not limited to these. Of these examples, preferred is tetrakistriphenylphenylphosphinopalladium.

Examples of the base to be used include lithium hydroxide, sodium hydroxide, potassium hydroxide, sodium carbonate, potassium carbonate, sodium acetate, potassium acetate, and further, triethylamine; however, sodium acetate and potassium acetate are preferred, which are milder.

A preferred solvent to be used is, for example, toluene or dioxane. The reaction temperature is preferably from room temperature to 150° C., more preferably from 80° C. to 120° C. The reaction period is preferably from 1 hour to 48 hours, more preferably from 2 hours to 24 hours.

(Step S-7)

Further, Step S-7 for converting the compound (407) to a compound (408) may be, for example, as follows, although not limited.

The compound (407) is dissolved into a solvent, and thereto is added an iodonium, such as Koser's reagent, under a nitrogen gas flow.

Examples of the solvent to be used include water, dichloromethane, acetone, acetonitrile, THF, methanol, ethanol, trifluoroethanol, and mixed solvents each composed of two or more kinds of these solvents. Among these, dichloromethane is preferred.

The reaction temperature is preferably from −20° C. to room temperature, more preferably from −10° C. to 5° C. The reaction period is preferably from 30 minutes to 2 hours.

(Step S-8)

A reagent used in Step S-8 for converting the compound (408) to a compound (409) may be, for example, hydrogen fluoride.

Examples of the solvent to be used include water, dichloromethane, acetone, acetonitrile, THF, methanol, ethanol, DMF, DMSO, and mixed solvents each composed of two or more kinds of these solvents. Of these examples, preferred is dichloromethane alone or a combination with acetonitrile, DMF, or DMSO.

The reaction temperature is preferably from −20° C. to 180° C., more preferably from 80° C. to 160° C. The reaction period is preferably from 5 minutes to 2 hours, more preferably from 10 minutes to 1 hour.

(Step S-9)

Step S-9 is a step of using a pinacol boronation reagent to produce a pinacol boric acid derivative from the compound 409 using a microwave radiation or the like in the presence of a palladium catalyst and a ligand. The catalyst to be used may be a palladium catalyst that is generally used in Suzuki-Miyaura coupling reaction, examples thereof including a palladium chloride cinnamyl complex, palladium acetate, and trisdibenzylideneacetonedipalladium, although the catalyst is not limited to these.

The microwave radiation conditions are preferably from room temperature to 200° C., more preferably from 80° C. to 180. The reaction period is preferably from 1 minute to 60 minutes, more preferably from 5 minutes to 30 minutes.

The ligand to be used may be a phosphorus-based ligand that is generally used in Suzuki-Miyaura coupling reaction, examples thereof including tricyclohexylphosphine, 2-dicyclohexylphosphino-2,4,6-triisopropylbiphenyl, 2-dicyclohexylphosphino-2,-(N,N)-dimethylaminobiphenyl, 3,5-dimethoxy-2-dicyclohexylphosphino-2,4,6-triisopropylbiphenyl, and 3,5-dimethoxy-2-ditert-butylphosphino-2,4,6-triisopropylbiphenyl, although the ligand is not limited to these.

Examples of the base to be used include lithium hydroxide, sodium hydroxide, potassium hydroxide, sodium carbonate, potassium carbonate, and further, triethylamine, although the base is not limited thereto. In particular, sodium carbonate and potassium carbonate are preferred, which are mild.

Preferred examples of the solvent to be used include toluene, dioxane, and DMDO.

(Step T-1)

Step T-1 is a step of producing a compound 502 by iodinating the compound 501. The method for iodination reaction may be, for example, a method of causing a metal perchlorate such as sodium perchlorate or sodium perchlorate to react with iodine or a metal iodide such as sodium iodide, or further a method of using an iodinating reagent such as N-iodosuccinimide in a strong acid such as sulfuric acid or trifluoromethanesulfonic acid.

(Step T-2)

Step T-2 is a step of using a protecting reagent for the compound (502) to protect an amino group thereof under basic conditions. The protecting reagent to be used may be, for example, benzyl chloroformate, or di-t-butyl dicarbonate, although the reagent is not limited to the exemplified compounds.

Preferred examples of the base to be used include lithium hydroxide, sodium hydroxide, potassium hydroxide, sodium carbonate, potassium carbonate, and further, triethylamine, although the base is not limited thereto. In particular, sodium carbonate and potassium carbonate are preferred, which are mild.

The solvent to be used is preferably an amphipathic solvent. In particular, examples thereof include acetone, acetonitrile, THF, DMF, and DMSO. The solvent is preferably acetone, acetonitrile, or THF in view of distilling off the solvent.

The reaction temperature is preferably from −20° C. to 100° C., more preferably from −4° C. to room temperature. The reaction period is preferably from 30 minutes to 24 hours, more preferably from 3 hours to 18 hours.

(Step T-3)

Step T-3 is a step of using a protecting reagent for the compound (503) to protect a carboxyl group thereof.

Examples of the solvent to be used include acetone, ethyl acetate, chloroform, THF, dioxane, methanol, and ethanol. Among these, methanol and ethanol are preferred, since these solvents are inactive to the reduction reaction.

The reaction temperature is preferably from −20° C. to 100° C., more preferably from room temperature to 50° C. The reaction period is preferably from 30 minutes to 24 hours, more preferably from 3 to 18 hours.

(Step T-4)

Step T-4 is a step of producing a compound 505 by reducing the compound 504 to turn the nitro group thereof into an amino group. Examples of the reducing agent include those causing reaction with an inorganic salt such as calcium chloride or an acid such as hydrochloric acid in the presence of iron, zinc, or tin, and further those reducing with a hydrogen gas in the presence of palladium, rubidium, ruthenium, or a complex thereof, although the reducing agent is not limited thereto.

Examples of the solvent to be used include acetone, acetonitrile, THF, methanol, and ethanol. Among these, methanol and ethanol are preferred, since these solvents are inactive to the reduction reaction.

The reaction temperature is preferably from −20° C. to 100° C., more preferably from room temperature to 50° C. The reaction period is preferably from 30 minutes to 24 hours, more preferably from 3 to 18 hours.

(Step T-5)

Step T-5 is a step of producing a halogen derivative (506) from the compound (505) via a diazonium. The diazonium reaction reagent may be, for example, sodium nitrite, potassium nitrite, or further an alkyl nitrite such as isobutyl nitrite. Also, the iodinating reagent may be, for example, sodium iodide, potassium iodide, or iodine, which is known.

Examples of the solvent to be used include water, acetone, acetonitrile, THF, methanol, ethanol, and mixed solvents each composed of two or more kinds of these solvents. Among these, acetone is preferred, since this solvent is inactive to the diazotization reaction.

The reaction temperature is preferably from −20° C. to room temperature, more preferably from −10° C. to 5° C. The reaction period is preferably from 30 minutes to 2 hours, more preferably from 30 minutes to 1 hour.

The halogen derivative (506) obtained in this manner is subjected to synthesis of a compound similar to the compound 410 in the same manner as in Steps S-6 to S-9.

(Step U-1 to Step U-4)

Further, Steps U-1 to U-4 are steps similar to Steps S-2 to S-5 and are steps of preparing compounds 601, 602, 603, 604, and 605.

(Step U-5)

Step U-5 is a step of subjecting the compound (605) to hydrogenating reduction to produce an aniline derivative. A catalyst to be used therefor is, for example, palladium hydroxide or palladium carbon, although the catalyst is not limited thereto.

Examples of the solvent to be used include acetone, acetonitrile, THF, methanol, and ethanol. Among these, methanol and ethanol are preferred, since these solvents are inactive to the reduction reaction.

The reaction temperature is preferably from −20° C. to 100° C., more preferably from room temperature to 50° C. The reaction period is preferably from 30 minutes to 24 hours, more preferably from 3 to 18 hours.

(Step U-6)

Step U-6 is a step of producing, from the compound (606), a triazene derivative (607) via a diazonium.

The diazonium reaction reagent to be used may be, for example, sodium nitrite, potassium nitrite, or further an alkyl nitrite such as isobutyl nitrite. Also, the reaction reagent may be, for example, dimethylamine, cyclopentylamine, or cyclohexylamine, which is known.

Examples of the solvent to be used include water, acetone, acetonitrile, THF, methanol, ethanol, and mixed solvents each composed of two or more kinds of these solvents. Among these, acetone is preferred, since this solvent is inactive to the diazotization reaction.

The reaction temperature is preferably from −20° C. to room temperature, more preferably from −10° C. to 5° C. The reaction period is preferably from 30 minutes to 2 hours, more preferably from 30 minutes to 1 hour. Also, from the compound (607) to (611) can be produced as well.

(Step U-7)

Step U-7 is a step of producing a halogen derivative (608) from the compound (606) via a diazonium. The diazonium reaction reagent may be, for example, sodium nitrite, potassium nitrite, or further an alkyl nitrite such as isobutyl nitrite. Also, the iodinating reagent may be, for example, sodium iodide, potassium iodide, or iodine, which is known.

Examples of the solvent to be used include water, acetone, acetonitrile, THF, methanol, ethanol, and mixed solvents each composed of two or more kinds of these solvents. Among these, acetone is preferred, since this solvent is inactive to the diazotization reaction.

The reaction temperature is preferably from −20° C. to room temperature, more preferably from −10° C. to 5° C. The reaction period is preferably from 30 minutes to 2 hours, more preferably from 30 minutes to 1 hour.

(Step U-8)

Step U-8 is a step of producing, from the compound (608), a trialkyltin compound (609) by a Suzuki-Miyaura coupling reaction. The reaction reagent to be used may be, for example, tributyltin or trimethyltin. The catalyst to be used may be a palladium catalyst that is generally used in Suzuki-Miyaura coupling reaction, examples thereof including a palladium chloride cinnamyl complex, palladium acetate, trisdibenzylideneacetonedipalladium, and tetrakistriphenylphenylphosphinopalladium, although the catalyst is not limited to these. Of these examples, preferred is tetrakistriphenylphenylphosphinopalladium.

Examples of the base to be used include lithium hydroxide, sodium hydroxide, potassium hydroxide, sodium carbonate, potassium carbonate, sodium acetate, potassium acetate, and further, triethylamine; however, sodium acetate and potassium acetate are preferred, which are milder.

A preferred solvent to be used is, for example, toluene or dioxane. The reaction temperature is preferably from room temperature to 150° C., more preferably from 80° C. to 120° C. The reaction period is preferably from 1 hour to 48 hours, more preferably from 2 hours to 24 hours.

(Step U-9)

For Step U-9 for converting the compound (609) to a compound (610), the following operation is given as an example, although an operation therefor is not limited.

The compound (609) is dissolved into a solvent, and thereto is then added an iodonium, such as Koser's reagent, under a nitrogen gas flow.

Examples of the solvent to be used include water, dichloromethane, acetone, acetonitrile, THF, methanol, ethanol, trifluoroethanol, and mixed solvents each composed of two or more kinds of these solvents. Among these, dichloromethane is preferred.

The reaction temperature is preferably from −20° C. to room temperature, more preferably from −10° C. to 5° C. The reaction period is preferably from 30 minutes to 2 hours.

(Step U-10)

A reagent used in step U-10 for converting the compound compound (610) to a compound (611) may be, for example, hydrogen fluoride.

Examples of the solvent to be used include water, dichloromethane, acetone, acetonitrile, THF, methanol, ethanol, DMF, DMSO, and mixed solvents each composed of two or more kinds of these solvents. Of these examples, preferred is dichloromethane alone or a combination with acetonitrile, DMF, or DMSO.

The reaction temperature is preferably from −20° C. to 180° C., more preferably from 80° C. to 160° C. The reaction period is preferably from 5 minutes to 2 hours, more preferably from 10 minutes to 1 hour.

(Step U-11)

Step U-11 is a step of using a pinacol boronation reagent to produce a pinacol boric acid derivative from the compound 611 using a microwave radiation in the presence of a palladium catalyst and a ligand by a method similar to that of Step S-9.

(Step U-12)

Step U-12 is a step of using a butoxycarbonylation reagent in the presence of DMAP to produce a di-Boc acid derivative from the compound (608).

Examples of the solvent to be used include toluene, dioxane, acetone, DMF, DMSO, and MeCN, although the solvent is not limited. In particular, acetone and MeCN are preferred.

The reaction temperature is preferably from room temperature to 100° C., more preferably from 30° C. to 60° C.

The reaction period is preferably from 8 hours to 48 hours, more preferably from 12 hours to 24 hours.

(Step U-13)

Step U-13 is a step of producing, from the compound (613), a trialkyltin compound (614) by a Suzuki-Miyaura coupling reaction. The reaction reagent to be used may be, for example, tributyltin or trimethyltin. The catalyst to be used may be a palladium catalyst that is generally used in Suzuki-Miyaura coupling reaction, examples thereof including a palladium chloride cinnamyl complex, palladium acetate, trisdibenzylideneacetonedipalladium, and tetrakistriphenylphenylphosphinopalladium, although the catalyst is not limited to these. Of these examples, preferred is tetrakistriphenylphenylphosphinopalladium.

Examples of the base to be used include lithium hydroxide, sodium hydroxide, potassium hydroxide, sodium carbonate, potassium carbonate, sodium acetate, potassium acetate, and further, triethylamine; however, sodium acetate and potassium acetate are preferred, which are milder.

A preferred solvent to be used is, for example, toluene or dioxane. The reaction temperature is preferably from room temperature to 150° C., more preferably from 80° C. to 120° C. The reaction period is preferably from 1 hour to 48 hours, more preferably from 2 hours to 24 hours.

(Step U-14)

Step U-14 is a step of obtaining a diaryliodonium salt (615) from the tin compound (614). For the present step, the following operation is given as an example, although an operation therefor is not particularly limited.

Production is made by adding an iodonium, such as Koser's reagent, to the tin compound (614) under a nitrogen gas flow.

Examples of the solvent to be used include water, dichloromethane, acetone, acetonitrile, THF, methanol, ethanol, 2,2,2-trifluoroethanol, 1,1,1,3,3,3-hexafluoroisopropanol, and mixed solvents each composed of two or more kinds of these solvents. Of these examples, preferred is dichloromethane, 2,2,2-trifluoroethanol, or 1,1,1,3,3,3-hexafluoroisopropanol.

The reaction temperature is preferably from −20° C. to 60° C., more preferably from −10° C. to room temperature. The reaction period is preferably from 30 minutes to 2 hours.

(Step U-15)

Step U-15 is a step of obtaining a fluorinated compound (616) from the diaryliodonium salt (615). Examples of the reagent to be used in Step U-15 include hydrogen fluoride, potassium fluoride, and cesium fluoride.

Examples of the solvent to be used include water, dichloromethane, acetone, acetonitrile, THF, methanol, ethanol, DMF, DMSO, and mixed solvents each composed of two or more kinds of these solvents. Of these examples, preferred is dichloromethane alone, acetonitrile alone, DMF alone, DMSO alone, or a combination of these.

The reaction temperature is preferably from −20° C. to 180° C., more preferably from 80° C. to 160° C. The reaction period is preferably from 5 minutes to 2 hours, more preferably from 10 minutes to 1 hour.

(Step U-16)

Step U-16 is a step of using a pinacol boronation reagent to produce a pinacol boric acid derivative from the compound (616) using a microwave radiation in the presence of a palladium catalyst and a ligand.

The catalyst to be used may be a palladium catalyst that is generally used in Suzuki-Miyaura coupling reaction, examples thereof including a palladium chloride cinnamyl complex, palladium acetate, and trisdibenzylideneacetonedipalladium, although the catalyst is not limited to these.

The microwave radiation conditions are preferably from room temperature to 200° C., more preferably from 80° C. to 180. The reaction period is preferably from 1 minute to 60 minutes, more preferably from 5 minutes to 30 minutes.

The ligand to be used may be a phosphorus-based ligand that is generally used in Suzuki-Miyaura coupling reaction, examples thereof including tricyclohexylphosphine, 2-dicyclohexylphosphino-2,4,6-triiso-propylbiphenyl, 2-dicyclohexylphosphino-2,-(N,N)-dimethylaminobiphenyl, 3,5-dimethoxy-2-dicyclohexylphosphino-2,4,6-triisopropylbiphenyl, and 3,5-dimethoxy-2-ditert-butylphosphino-2,4,6-triisopropylbiphenyl, although the ligand is not limited to these.

Examples of the base to be used include lithium hydroxide, sodium hydroxide, potassium hydroxide, sodium carbonate, potassium carbonate, and further, triethylamine, although the base is not limited thereto. In particular, sodium carbonate and potassium carbonate are preferred, which are mild.

Preferred examples of the solvent to be used include toluene, dioxane, and DMDO.

(Step U-17)

Step U-17 is a step of subjecting the compound (615) to salt exchange reaction for substituting counter-anions, so as to obtain a compound (618). The reaction reagent may be, for example, sodium chloride or potassium bromide.

(Step U-18)

Examples of the reagent to be used in Step U-18 include hydrogen fluoride, potassium fluoride, and cesium fluoride.

Examples of the solvent to be used include water, dichloromethane, acetone, acetonitrile, THF, methanol, ethanol, DMF, DMSO, and mixed solvents each composed of two or more kinds of these solvents. Of these examples, preferred is dichloromethane alone, acetonitrile alone, DMF alone, DMSO alone, or a combination of these.

The reaction temperature is preferably from −20° C. to 180° C., more preferably from 80° C. to 160° C. The reaction period is preferably from 5 minutes to 2 hours, more preferably from 10 minutes to 1 hour.

(Step U-19)

Step U-19 is a step of using a pinacol boronation reagent to produce a pinacol boric acid derivative from the compound (608) in the presence of a palladium catalyst and a ligand. The catalyst to be used may be a palladium catalyst that is generally used in Suzuki-Miyaura coupling reaction, examples thereof including dichlorobis(triphenylphosphine)palladium, a palladium chloride cinnamyl complex, palladium acetate, and trisdibenzylideneacetonedipalladium, although the catalyst is not limited to these.

The ligand to be used may be a phosphorus-based ligand that is generally used in Suzuki-Miyaura coupling reaction, examples thereof including tricyclohexylphosphine, 2-dicyclohexylphosphino-2,4,6-triiso-propylbiphenyl, 2-dicyclohexylphosphino-2,-(N,N)-dimethylaminobiphenyl, 3,5-dimethoxy-2-dicyclohexylphosphino-2,4,6-triisopropylbiphenyl, and 3,5-dimethoxy-2-ditert-butylphosphino-2,4,6-triisopropylbiphenyl, although the ligand is not limited to these.

Examples of the base to be used include sodium acetate, potassium acetate, lithium hydroxide, sodium carbonate, potassium carbonate, and further, triethylamine, although the base is not limited thereto. In particular, sodium acetate and potassium acetate are preferred, which are mild.

Preferred examples of the solvent to be used include toluene, dioxane, and DMSO. The reaction temperature is preferably from room temperature to 150° C., more preferably from 80° C. to 120° C.

The reaction period is preferably from 30 minutes to 48 hours, more preferably from 2 hours to 18 hours.

(Step U-20)

Step U-20 is a step of causing the compound (619) to react with a fluorination reagent in the presence of a copper catalyst to obtain a compound (616). The fluorination reagent to be used may be, for example, hydrogen fluoride or potassium fluoride.

Examples of the solvent to be used include toluene, dioxane, DMF, DMSO, and MeCN, among which DMF and MeCN are preferred.

The reaction temperature is preferably from room temperature to 150° C., more preferably from 80° C. to 120° C.

The reaction period is preferably from 1 minute to 60 minutes, more preferably from 5 minutes to 30 minutes.

(Step V-1 to Step V-4)

Steps V-1 to V-4 are steps similar to Steps S-2 to S-5 and are steps of preparing compounds 701, 702, 703, 704, and 705.

(Step V-5)

Further, Step V-5 is similar to Step U-11.

When F is contained in the compound in each derivative, labeling can be carried out with $^{18}$F instead of F.

For example, accelerated protons may be radiated onto $H_2{}^{18}O$ to synthesize $H^{18}F$-hydrofluoric acid through $^{18}O$ (p, n) reaction, and then this acid may be passed through an ion exchange resin column to be adsorbed thereon to separate this acid from $H_2{}^{18}O$ which is a non-adsorbed raw material. This column is subjected to elution with an aqueous solution of $K_2CO_3$ to yield $K^{+18}F^-$, which can be used as a nucleophilic agent.

[Formula 16]

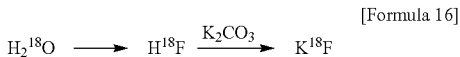

When $N=N-NR_7R_8$ is present before fluorination among the compounds in the present invention, labeling with $^{18}$F can be achieved by a known method. That is, the obtained $^{18}$F anions are used as a nucleophilic agent, and the anions are heated together with a phase transfer catalyst in an organic solvent, thereby yielding a labeled body.

Further, with respect to $Sn(R_6)_3$, the labeled body is obtained by a technique of Ermert and others (Non-Patent Document: J. Label. Compd. Radiopharm., 47, 429, 2004.). In other words, the labeled body is yielded with a good efficiency by causing reaction with hydroxyl(tosyloxy)Iodoarene, such as Koser's reagent, to produce a diallyliodonium salt temporarily, and then causing this salt to react with a nucleophilic agent $^{18}$F.

Furthermore, each protecting group can be de-protected by a conventional method, whereby the target fluorinated BPA can be prepared.

By using the method of the present invention, such $^{18}$F-labeled compound can be obtained with a comparatively good yield and in a state having a good specific activity.

EXAMPLES

The present invention will be described in more detail by way of the following Examples; however, such inventions are not limited to this alone.

Here, in the Examples described below, the following machines and reagents were used for analyzing compounds and isolating/purifying the compounds.

NMR spectrum: JNM-AL series AL400 manufactured by JEOL Ltd. at 400 MHz

Microwave radiation: Initiator+ manufactured by Biotage

UPLC analysis: ACQUITY UPLC system manufactured by Nihon Waters K.K.

Example 1

Production of 4-bromo-2-iodotoluene

Into 30% sulfuric acid (100 mL), 4-bromo-2-aminotoluene (10.0 g, 53.7 mmol) was suspended. To this, an aqueous solution (15 mL) of sodium nitrite (3.89 g, 56.4 mmol) was dropwise added slowly from a dropping funnel while the system was being cooled with ice. The resultant was stirred at 0° C. for 45 minutes. Thereafter, sodium iodide (12.1 g, 80.6 mmol) was dissolved into water (50 mL). To this aqueous solution was added the above-mentioned diazonium salt solution. The resultant was stirred further for 1 hour at room temperature, and then was subjected to extraction with ethyl acetate for 3 times. Subsequently, the ethyl acetate layer was washed with a saturated saline solution once, then dried over magnesium sulfate, and concentrated under a reduced pressure. Thereafter, the resultant was purified with a silica gel column (n-hexane) to yield the target compound (9.0 g, 45%).

$^1$H-NMR(CDCl$_3$); 2.37(s, 3H, CH$_3$), 7.08(d, J=8.0, 1H, Ar), 7.35(dd, J=1.6, 8.0, 1H, Ar), 7.93(d, J=2.0, 1H, Ar).

Production of 4-bromo-2-iodobenzyl bromide

To carbon tetrachloride (100 mL) were added 4-bromo-2-iodotoluene (9.00 g, 23.9 mmol) obtained in the previous step, N-bromosuccinimide (5.95 g, 33.5 mmol), and 2,2-azobis(2-methylpropionitrile) (39 mg, 2.4 mmol) to cause the reactants to react with each other for 18 hours while the reaction system was refluxed. Thereafter, the reaction liquid was filtrated, and the resultant filtrate was concentrated under a reduced pressure. The resultant was purified through silica gel column chromatography (n-hexane) to yield 7.0 g of the target compound (78%).

$^1$H-NMR(CDCl$_3$); 4.53(s, 2H, CH$_2$), 7.32(d, J=8.0, 1H, Ar), 7.46(dd, J=2.0, 8.4, 1H, Ar), 7.93(d, J=2.0, 1H, Ar).

Production of benzyl 3-(4-bromo-2-iodophenyl)-2-(diphenylmethyleneamino)propanoate To toluene (100 mL) were added cesium hydroxide (7.54 g, 50.3 mmol), benzyl N-(diphenylmethylene)glycinate (5.50 g, 16.7 mmol), and O-allyl-N-9-anthracenylmethyl-cinchonidium bromide (1.10 g, 1.67 mmol, 0.1 equiv). The resultant was cooled to 0° C. Thereafter, while this toluene mixture solution was being violently stirred, a toluene (10 mL) solution of the compound (6.30 g, 16.7 mmol) obtained in the previous step was added all at a time. After the end of dropwise addition, the resultant was stirred for 18 hours while being kept as it was. Thereafter, the reaction solution was subjected to extraction with ether (50 ml) for two times, and further, this ether layer was washed with a saturated saline solution, then dried over magnesium sulfate, and concentrated under a reduced pressure, thereby to yield a crude target compound (8.7 g). This compound was subjected to the next step without being purified.

Production of benzyl 2-amino-3-(4-bromo-2-iodophenyl)propanoate

The compound benzyl 3-(4-bromo-2-iodophenyl)-2-(diphenylmethyleneamino)propanoate (8.6 g) obtained in the previous step was dissolved into THF (86 mL), and further, a 30% aqueous solution of citric acid (50 mL) was added thereto. This mixture solution was caused to undergo a reaction under reflux for 1 hour. After the end of the reaction, the reaction solution was washed with ether (80 mL), and then neutralized with potassium carbonate. Thereafter, the resultant was subjected to extraction with EtOAc (80 mL) for two times, dried over magnesium sulfate, and then concentrated under a reduced pressure. Further, the resultant was purified through silica gel column chromatography (AcOEt/n-hexane=1/1) to yield the target compound (2.40 g, with a yield of 31%).

$^1$H-NMR(CDCl$_3$); 2.90(dd, J=8.4, 13.6, 1H, CH$_2$-α), 3.18 (dd, J=6.4, 13.6, 1H, CH$_2$-β), 3.83(dd, J=6.4, 8.2, 1H, CH), 5.14(m, 2H, CH$_2$Ar), 7.01(d, J=8.4, 1H, Ar), 7.26-7.39(m, J=6.0, 8.4, 1H, Ar), 7.96(d, J=2.4, 1H, Ar).

Production of benzyl 3-(2-bromo-4-iodophenyl)-2-(benzyloxycarbonylamino)propanoate The above-mentioned compound benzyl 2-amino-3-(4-bromo-2-iodophenyl)propanoate (2.32 g, 5.44 mmol) was dissolved into THF (50 mL). Thereto were added H$_2$O (50 mL) and K$_2$CO$_3$ (903 mg, 6.53 mmol), and the resultant was stirred while the system was being cooled with ice. Thereinto, a solution obtained by adding benzyl chloroformate (1.11 g, 6.53 mmol) to acetonitrile (10 mL) was slowly added, and the resultant was stirred at room temperature for 12 hours. The reaction solution is subjected to extraction with AcOEt (50 mL) for three times, and the organic layer is washed with a 10% aqueous solution of citric acid (50 mL) for three times and further with a saturated saline solution (50 mL) for two times, followed by drying over MgSO$_4$. After the organic layer was concentrated, the resultant was purified through flash column chromatography (hexane:AcOEt=6:1) to yield the target compound as a colorless oily substance (2.68 g, 83%).

$^1$H-NMR(CDCl$_3$); 3.10(dd, J=8.0, 14.8, 1H, CH$_2$-α), 3.26 (dd, J=6.4, 14.8, 1H, CH$_2$-β), 4.73(m, 1H, CH), 5.06(m, 2H, CH$_2$Ar), 5.15(s, 2H, CH$_2$Ar), 5.30(m, J=8.0, 1H, NH), 7.24-7.36(m, 11H, Ar), 7.91(d, J=1.7, 1H, Ar).

Production of benzyl 2-(benzyloxycarbonylamino)-3-(4-bromo-2-(tri-n-butylstannyl)phenyl)propanoate PdCl$_2$(dppf) (40 mg, 0.049 mmol), bis(tributyltin) (627 mg, 1.08 mmol), and potassium acetate were dissolved into DMSO (5 mL) in an Ar atmosphere, and the resultant was kept being stirred at room temperature. After a DMSO solution (2 mL) of the above-mentioned compound benzyl 3-(2-bromo-4-iodophenyl)-2-(benzyloxycarbonylamino) propanoate (515 mg, 0.979 mmol) was added thereinto, the resultant was stirred at 80° C. for 24 hours. The reaction solution was diluted with ethyl acetate (70 mL) and subjected to Celite filtration. Thereafter, the resultant was washed with water and a saline solution, and the organic layer was dried over MgSO$_4$. The organic layer was filtrated, and the organic solvent was concentrated and then purified through column chromatography (hexane:ethyl acetate=9:1) to yield the target compound as a colorless oily substance (381 mg, 74%).

$^1$H-NMR(CDCl$_3$); 0.85(t, J=7.6, 9H, —CH$_2$CH$_2$CH$_3$×3), 1.05(m, 6H, -CH$_2$CH$_2$CH$_3$×3), 1.27-1.45(m, 6H, —CH$_2$CH$_2$CH$_3$×3), 3.01(dd, J=9.2, 14.4, 1H, CH$_2$-α), 3.48(dd, J=4.4, 14.4, 1H, CH$_2$-β), 4.53(m, 1H, CH), 5.04(s, 2H, CH$_2$Ar), 5.20(m, 2H, CH$_2$Ar), 6.95(d, J=7.6, 1H, Ar), 7.10-7.44(m, 12H, Ar).

Production of (2-(3benzyloxy-2-(benzyloxycarbonylamino)-3-oxopropyl)-5-bromophenyl)(3-methoxyphenyl)iodonium tosylate Trifluoroethanol (2 mL) was added to the above-mentioned compound benzyl 2-(benzyloxycarbonylamino)-3-(4-bromo-2-(tri-n-butylstannyl)phenyl)propanoate (154 mg, 0.228 mmol), and the resultant was stirred in an ice water bath under a nitrogen gas flow for 1 hour. Thereto was added an iodonium salt (96.10 mg, 0.228 mmol) while the system was being cooled with ice. The resultant was stirred for 15 minutes in an ice water bath. From the reaction mixture liquid, the solvent was distilled off at room temperature. Hexane (10 mL) was added to the obtained mixture, and the mixture was washed and subjected to decantation to remove the solution part. The same operation was carried out for two times, and the residual solvent in the obtained mixture was completely removed under a reduced pressure, thereby to obtain a target compound (159 mg, 80%).

$^1$H-NMR(DMSO-$d_6$); 2.29(s, 3H, TsOH—CH$_3$), 3.23(dd, J=10.8, 14.8, 1H, CH$_2$-α), 3.39(m, 1H, CH$_2$-β, overlapped with water), 3.75(s, 3H, —OCH$_3$), 4.51(m, 1H, CH), 5.00 (m, 2H, BnCH$_2$), 5.17(s, 2H, BnCH$_2$), 7.12(d, J=8.0, 2H, TsOH-Ar), 7.19-8.06(m, 19H, Ar).

Production of benzyl 2-(benzyloxycarbonylamino)-3-(4-bromo-2-fluorophenyl)propanoate The above-mentioned compound (2-(3benzyloxy-2-(benzyloxycarbonylamino)-3-oxopropyl)-5-bromophenyl)(3-methoxyphenyl)iodonium tosylate (100 mg, 0.115 mmol), kryptofix 2.2.2 (43.1 mg, 0.115 mmol), and potassium fluoride (6.7 mg, 0.115 mmol) were stirred in DMF (10 mL) at 100° C. for 15 minutes. After the end of the reaction, the solvent was distilled off under a reduced pressure, and the obtained residue was purified through silica gel column chromatography (hexane:AcOEt=7:1) to yield the target compound (34.0 mg, 61%).

$^1$H-NMR(CDCl$_3$); 3.05(dd, J=6.4, 14.0, 1H, CH$_2$-α), 3.16 (dd, J=5.6, 14.0, 1H, CH$_2$-β), 4.67(m, 1H, CH), 5.08(m, 2H, BnCH$_2$), 5.13(s, 2H, BnCH$_2$), 5.31(d, J=8.0, 1H, NH), 6.86(m, 1H, Ar), 7.09-7.15(m, 2H, Ar), 7.26-7.37(m, 10H, Ar).

Production of benzyl 2-(benzyloxycarbonylamino)-3-(2-fluoro-4-(4,4,5,5-tetramethyl-1,3,2-dioxaborolane-2-yl)phenyl)-propanoate Under a nitrogen gas flow, PdCl$_2$(dba) (27.5 mg, 0.03 eq.) and tricyclophosphine (16.8 mg, 0.06 eq.) were suspended in dioxane (5 ml). After stirring for 30 minutes, bis(pinacolate) diborane (305 mg, 1.20 mmol) and KOAc (294 mg, 3.00 mmol) were added, and further the above-mentioned compound benzyl 2-(benzyloxycarbonylamino)-3-(4-bromo-2-fluorophenyl)propanoate (486 mg, 1.00 mmol) was added. Thereafter, microwave radiation was carried out at 150° C. for 15 minutes to yield the target compound (421 mg, 79%).

$^1$H-NMR(CDCl$_3$); 3.14(dd, J=8.8, 13.6, 1H, CH$_2$-α), 3.20 (dd, J=5.2, 13.6, 1H, CH$_2$-β), 4.69(m, 1H, CH), 5.08(m, 1H, BnCH$_2$), 5.14(s, 1H, BnCH$_2$), 5.30(d, J=8.0, NH), 7.05(t, J=7.3, 1H, Ar), 7.26-7.50(m, 12H, Ar).

Example 2

Production of tert-butyl 2-(tert-butoxycarbonylamino)-3-(2-iodo-4-nitrophenyl)propanoate Into trifluoromethanesulfonic acid (5 mL), 4-nitrophenylalanine (1.00 g, 4.76 mmol) was dissolved. To this, N-iodosuccinimide (963 mg, 0.9 eq.) was added in three parts in 15 minutes. Further, the resultant was caused to react at room temperature for 18 hours.

Thereafter, the above-mentioned reaction liquid was added to ice water, and the pH value was set to be 12 or more with potassium carbonate. Further, an acetonitrile solution (about 10 mL) of Boc$_2$O (1.25 g, 5.71 mmol) was added, and the mixture was stirred at room temperature for 18 hours.

After the end of the reaction, the pH value was set to be 4 or less with citric acid, and the resultant was subjected to extraction with ethyl acetate (50 mL) for three times. Further, this organic layer was washed with water (100 mL) and a saturated saline solution (100 mL). The resultant was dried over magnesium sulfate and thereafter concentrated under a reduced pressure to yield an intermediate crude product. Further, this crude product 503 was dissolved in tert-BuOH (20 mL), and Boc$_2$O (1.25 g, 5.71 mmol) was added. Subsequently, DMAP (116 mg, 0.951 mmol) was added. Thereafter, the resultant is stirred at room temperature for 18 hours. After the end of the reaction, the solvent was distilled off under a reduced pressure, and then the resultant was purified through silica gel column chromatography to yield the target compound tert-butyl 2-(tert-butoxycarbonylamino)-3-(2-iodo-4-nitrophenyl)propanoate (1.26 g, 54%).

$^1$H-NMR(CDCl$_3$); 1.35(s, 12H, 9H, t-Bu), 1.42(s, 9H, t-Bu), 3.10(dd, J=8.4, 13.6, 1H, CH$_2$-α), 3.18(dd, J=6.4, 13.6, 1H, CH$_2$-β), 3.83(dd, J=6.4, 8.2, 1H, CH), 5.14(m, 2H, CH$_2$Ar), 7.41(d, J=8.4, 1H, Ar), 8.13(dd, J=2.0, 8.4, 1H, Ar), 8.68(d, J=2.0, 1H, Ar).

Production of tert-butyl 2-(tert-butoxycarbonylamino)-3-(4-amino-2-iodophenyl)propanoate The above-mentioned compound tert-butyl 2-(tert-butoxycarbonylamino)-3-(2-iodo-4-nitrophenyl)propanoate (2.32 g, 4.71 mmol) was dissolved into ethanol (23 mL), and further iron powder (0.657 g, 2.5 eq.) was added. Thereafter, the temperature was raised to 80° C. Subsequently, an aqueous solution obtained by dissolving ammonium chloride (0.252 g, 1.0 eq.) into water (2 mL) was added all at a time. Further, the resultant was caused to react at 80° C. for 1 hour. After the end of the reaction, iron powder and the like were filtrated, and thereafter the filtrate was concentrated under a reduced pressure. The concentrate was dissolved in ethyl acetate (50 mL) and washed with water (50 mL) and a saturated saline solution (50 mL). The resultant was dried over magnesium sulfate and then filtrated. Thereafter, the filtrate was concentrated under a reduced pressure. This residue was purified through silica gel column chromatography (AcOEt/n-hexane=1/2) to yield the target compound (1.00 g, 46%).

$^1$H-NMR(CDCl$_3$); 1.39(s, 9H, t-Bu), 1.42(s, 9H, t-Bu), 2.92(dd, J=7.2, 14.0, 1H, CH$_2$-α), 3.11(dd, J=5.6, 14.0, 1H, CH$_2$-β), 4.45(m, 1H, CH), 4.99(m, J=8.4, 1H, NH), 6.59(dd, J=2.4, 8.4, 1H, Ar), 6.95(d, J=8.4, 1H, Ar), 7.18(d, J=2.4, 1H, Ar).

Production of tert-butyl 2-(tert-butoxycarbonylamino)-3-(4-bromo-2-iodophenyl)propanoate The above-mentioned compound tert-butyl 2-(tert-butoxycarbonylamino)-3-(4-amino-2-iodophenyl)propanoate (2.5 g, 5.41 mmol) was subjected to conventional Sandmeyer's reaction to yield the target brominated compound tert-butyl 2-(tert-butoxycarbonylamino)-3-(4-bromo-2-iodophenyl)propanoate (1.56 g, 55%).

$^1$H-NMR(CDCl$_3$); 1.37(s, 9H, t-Bu), 1.43(s, 9H, t-Bu), 2.98(dd, J=8.4, 13.6, 1H, CH$_2$-α), 3.20(dd, J=5.6, 14.0, 1H, CH$_2$-β), 4.51(m, 1H, CH), 5.04(d, J=9.2, 1H, NH), 7.10(d, J=8.0, 1H, NH), 7.39(dd, J=1.6, 8.0, 1H, Ar), 7.97(d, J=1.6, 1H, Ar).

Further, a pinacol boronated compound can be prepared by using the compound tert-butyl 2-(tert-butoxycarbonylamino)-3-(4-bromo-2-iodophenyl)propanoate in the same manner as in Example 1.

Example 3

Production of 4-bromo-2-nitrobenzyl bromide

The target compound 4-bromo-2-nitrobenzyl bromide was obtained by a method similar to that of the bromination of Example 1 described above.

$^1$H-NMR(CDCl$_3$); 4.78(s, 2H, CH$_2$), 7.46(d, J=8.0, 1H, Ar), 7.74(m, J=2.0, 8.1, 1H, Ar), 8.18(d, J=1.7, 1H, Ar).

Production of tert-butyl 2-amino-3-(4-bromo-2-nitrophenyl)propanoate

The target compound was obtained by a method similar to that of the production of benzyl 3-(4-bromo-2-iodophenyl)-2-(diphenylmethyleneamino)propanoate and benzyl 2-amino-3-(4-bromo-2-iodophenyl)propanoate in Example 1.

$^1$H-NMR(CDCl$_3$); 1.45(s, 9H, t-Bu), 3.08(dd, J=8.8, 13.6, 1H, CH$_2$-α), 3.29(dd, J=5.6, 13.6, 1H, CH$_2$-β), 3.62(dd, J=5.6, 8.5, 1H, CH), 7.31(d, J=8.4, 1H, Ar), 7.66(dd, J=2.0, 8.4, 1H, Ar), 8.10(d, J=2.0, 1H, Ar).

Production of tert-butyl 3-(4-bromo-2-nitrophenyl)-2-(tert-butoxycarbonylamino)propanoate The target compound was obtained by an amino-group protection reaction similar to that of Example 1 by using tert-butyl N-(diphenylmethylene)glycinate and the compound obtained in the previous step as starting materials.

$^1$H-NMR(CDCl$_3$); 1.37(s, 9H, t-Bu), 1.44(s, 9H, t-Bu), 3.08(dd, J=8.0, 13.2, 1H, CH$_2$-α), 3.29(dd, J=5.2, 13.5, 1H, CH$_2$-β), 4.54(m, 1H, CH), 5.15(d, J=8.0, 1H, NH), 7.29(d, J=8.4, 1H, Ar), 7.65(dd, J=1.7, 8.0, 1H, Ar), 8.11(d, J=1.7, 1H, Ar).

Production of tert-butyl 3-(2-amino-4-bromophenyl)-2-(tert-butoxycarbonylamino)propanoate The compound obtained in the previous step (1.0 g, 2.25 mmol) was dissolved into ethanol (10 mL), and further iron powder (0.314 g, 2.5 eq.) was added. Thereafter, the temperature was raised to 80° C. Subsequently, an aqueous solution obtained by dissolving ammonium chloride (0.120 g, 1.0 eq.) into water (2 mL) was added all at a time. Further, the resultant was caused to react at 80° C. for 1 hour. After the end of the reaction, iron powder and the like were filtrated, and thereafter the filtrate was concentrated under a reduced pressure. The concentrate was dissolved in ethyl acetate (50 mL) and washed with water (50 mL) and a saturated saline solution (50 mL). The resultant was dried over magnesium sulfate and then filtrated. Thereafter, the filtrate was concentrated under a reduced pressure. This residue was purified through silica gel column chromatography (AcOEt/n-hexane=1/2) to yield the target compound 606 (0.457 g, 49%).

$^1$H-NMR(CDCl$_3$); 1.34(s, 9H, t-Bu), 1.44(s, 9H, t-Bu), 2.77(dd, J=8.8, 14.0, 1H, CH$_2$-α), 3.14(dd, J=3.6, 13.6, 1H, CH$_2$-β), 4.59(m, 1H, CH), 5.41(d, J=8.0, 1H, NH), 6.56(d, J=1.7, 1H, Ar), 6.86(d, J=8.0, 1H, Ar), 7.03(dd, J=1.6, 8.0, 1H, Ar).

Production of tert-butyl 3-(4-bromo-2-(pyrrolidine-1-yldiazenyl)phenyl)-2-(tert-butoxycarbonylamino)propanoate The compound obtained in the previous step (60.0 mg, 0.144 mmol) is dissolved in MeCN (2 mL), and further water (5 mL) is added. Thereafter, the resultant is cooled to 0° C., and further 12N HCl (1.2 mL) is added. While 0° C. is maintained, sodium nitrite (10.5 mg, 0.152 mmol) dissolved in water (1 mL) is dropwise added. After the dropwise addition, the resultant is further stirred at 0° C. for 30 minutes.

While 0° C. is maintained, the above-mentioned diazonium hydrochloride is dropwise added into a mixture solution which is separately obtained in advance by dissolving pyrrolidine (12.8 mg, 0.181 mmol) and potassium carbonate (100 mg, 0.722 mmol) into MeCN (5 mL) and water (10 mL). Further, the resultant is stirred at 0° C. for 30 minutes and then subjected to extraction with chloroform (20 mL) for two times. The chloroform layer is washed with water (15 mL) and a saturated saline solution (15 mL) and then dried over magnesium sulfate. After filtration, the filtrate is concentrated under a reduced pressure. The obtained residue is purified through silica gel column chromatography to yield the target compound (32.3 mg, 45%).

$^1$H-NMR(CDCl$_3$); 1.37(s, 9H, t-Bu), 1.39(s, 9H, t-Bu), 2.05(brs, 4H, pyrrolidines-CH$_2$CH$_2$—), 3.06(dd, J=9.2, 13.2, 1H, CH$_2$-α), 3.16(dd, J=4.0, 13.2, 1H, CH$_2$-β), 3.76 (brs, 2H, pyrrolidines-NCH$_2$—), 3.97(brs, 2H, pyrrolidines-NCH$_2$—), 4.31(m, 1H, CH), 6.47(d, J=6.4, 1H, NH), 7.04(d, J=8.0, 1H, Ar), 7.16(dd, J=2.0, 8.0, 1H, Ar), 7.56(d, J=2.0, 1H, Ar).

Production of tert-butyl 3-(4-bromo-2-iodophenyl)-2-(tert-butoxycarbonylamino)propanoate The target compound was obtained from tert-butyl 3-(2-amino-4-bromophenyl)-2-(tert-butoxycarbonylamino)propanoate by a step similar to that of the reaction using N-iodosuccinimide in Example 1.

$^1$H-NMR(CDCl$_3$); 1.37(s, 9H, t-Bu), 1.43(s, 9H, t-Bu), 2.98(dd, J=8.4, 13.6, 1H, CH$_2$-α), 3.20(dd, J=5.6, 14.0, 1H, CH$_2$-β), 4.51(m, 1H, CH), 5.04(d, J=9.2, 1H, NH), 7.10(d, J=8.0, 1H, NH), 7.39(dd, J=1.6, 8.0, 1H, Ar), 7.97(d, J=1.6, 1H, Ar).

Production of tert-butyl 3-(4-bromo-2-fluorophenyl)-2-(tert-butoxycarbonylamino)propanoate The target compound was obtained by a method similar to that of Steps S-6 to S-8.

$^1$H-NMR(CDCl$_3$); 1.37(s, 18H, t-Bux2), 2.98(dd, J=6.8, 14.0, 1H, CH$_2$-α), 3.10(dd, J=6.4, 14.0, 1H, CH$_2$-β), 4.43 (m, 1H, CH), 5.08(d, J=7.6, 1H, NH), 7.09(t, J=8.0, 1H, Ar), 7.20(d, J=8.4, 1H, Ar), 7.21(d, J=8.4, 1H, Ar).

Production of tert-butyl 2-(tert-butoxycarbonylamino)-3-(2-fluoro-4-(4,4,5,5-tetramethyl1,3,2dioxaborolane-2-yl)phenyl)-propanoate Under a nitrogen gas flow, PdCl$_2$(dba) (27.5 mg, 0.03 eq.) and tricyclophosphine (16.8 mg, 0.06 eq.) were suspended in dioxane (5 ml). After stirring for 30 minutes, bis(pinacolate) diborane (305 mg, 1.20 mmol) and KOAc (294 mg, 3.00 mmol) were added, and further the above-mentioned compound 611 (418 mg, 1.00 mmol) was added. Thereafter, microwave radiation was carried out at 150° C. for 15 minutes to yield the target compound (372 mg, 80%).

$^1$H-NMR(CDCl$_3$); 1.33(s, 9H, -Boc), 1.40(s, 21H, t-Bu, pinacol(CH$_3$)$_4$), 3.06(dd, J=8.8, 13.6, 1H, CH$_2$-α), 3.16(dd, J=5.2, 13.6, 1H, CH$_2$-β), 4.45(m, 1H, CH), 5.04(d, J=8.0, 1H, NH), 7.20(m, J=6.7, 7.6, 1H, Ar), 7.42-7.50(m, 2H, Ar).

Example 4

Production of tert-butyl 2-(bis(tert-butoxycarbonyl)amino)-3-(4-bromo-2-iodophenyl)propanoate The compound tert-butyl 3-(4-bromo-2-iodophenyl)-2-(tert-butoxycarbonylamino)propanoate (1.50 g, 2.6 mmol) is dissolved into MeCN (15 mL), and Boc$_2$O (1.16 g, 5.33 mmol) and further DMAP (488 mg, 4.00 mmol) are added thereto. The resultant is heated to 50° C. and caused to react at this temperature for 24 hours. Thereafter, the solvent is concentrated under a reduced pressure and then purified through silica gel column chromatography (hexane:ethyl acetate=9:1) to yield the target compound as a colorless oily substance. (1.50 g, 90%).

$^1$H-NMR(CDCl$_3$); 1.34-1.41(m, 27H, t-Bu), 3.35(dd, J=11.2, 13.6, 1H, CH$_2$-α), 3.46(dd, J=4.4, 14.0, 1H, CH$_2$-β), 5.08(dd, J=4.0, 11.2, 1H, CH), 7.00(d, J=8.0, 1H, Ar), 7.36(dd, J=2.0, 8.0, 1H, Ar), 7.94(d, J=2.0, 1H, Ar).

Production of tert-butyl 2-(bis(tert-butoxycarbonyl)amino)-3-(4-bromo-2-(trimethylstannyl)phenyl)propanoate The compound obtained in the previous step (876.8 mg, 1.40 mmol) is dissolved into toluene (4 mL), and tetrakistriphenylphosphinepalladium (80.88 mg, 0.07 mmol) and further bis(trimethyltin) (481.6 mg, 1.47 mmol) are added thereto. The resultant is heated to 120° C. and caused to react at this temperature for 3 hours. Thereafter, the solvent is concentrated under a reduced pressure and then purified through silica gel column chromatography (hexane:ethyl acetate=100:0 to 95:5) to yield the target compound as a colorless oily substance. (803.3 mg, 86.5%).

$^1$H-NMR(CDCl$_3$); 0.36(s, 9H, SnCH$_3$×3), 1.39(s, 18H, -Boc), 1.48(s, 9H, t-Bu), 3.28(d, J=7.6, 2H, CH$_2$), 4.84(t, J=7.6, 1H, CH), 6.95(d, J=8.4, 1H, Ar), 7.33(dd, J=2.0, 8.4, 1H, Ar), 7.48(d, J=2.0, 1H, Ar).

Production of (2-(3-tert-butoxy-2-(benzyloxycarbonylamino)-3-oxopropyl)-5-bromophenyl)(4-methylphenyl)iodonium tosylate The compound obtained in the previous step (663 mg, 1.00 mmol) is dissolved into 2,2,2-trifluoroethanol (40 mL), and 4-(hydroxy(tosyloxy)iodo)toluene (406 mg, 1.00 mmol) is added thereto. The resultant is caused to react at room temperature for 15 minutes. Extraction with diethyl ether is carried out, and the diethyl ether layer is dried over magnesium sulfate. After filtration, the resultant is concentrated under a reduced pressure, and the obtained residue is purified through silica gel column chromatography (hexane:ethyl acetate=100:1 to 10:1) to yield the target compound (180 mg, 20%).

$^1$H-NMR(CDCl$_3$); 1.35-1.47(m, 27H, t-Bu), 2.32(s, 3H, TsO-CH$_3$), 2.37(s, 3H, Ar—CH$_3$), 3.38(dd, J=8.0, 14.4, 1H, CH$_2$-α), 3.59(dd, J=7.2, 14.4, 1H, CH$_2$-β), 5.05(t, J=7.6, 1H, CH), 7.06(d, J=8.0, 2H, TsO—Ar), 7.18(d, J=8.4, 2H, Ar), 7.28(d, J=8.4, 1H, Ar), 7.53(dd, J=1.6, 8.4, 1H, Ar), 7.61(d, J=8.0, 2H, TsO—Ar), 7.87(d, J=1.6, 1H, Ar), 7.91(d, J=8.4, 2H, Ar).

Production of tert-butyl 2-(bis(tert-butoxycarbonyl)amino)-3-(2-fluoro-4-bromophenyl)propanoate Into MeCN (4 mL), 4,7,13,16,21,24-hexaoxa-1,10-diazabicyclo[8.8.8]hexacosane (14.24 mg, 0.04 mmol) is dissolved, and potassium fluoride (2.2 mg, 0.04 mmol) is added. The resultant is concentrated at 60° C. under a reduced pressure. The same operation is repeated for three times, and thereafter the resultant is dried for 12 hours under a reduced pressure with a vacuum pump. To the obtained mixture, 2,2,6,6-tetramethylpiperidine 1-oxyl (1 mg) is added, and further a DMF solution (1 mL) of the compound 615 (28.0 mg, 0.03 mmol) is added. The resultant is heated to 140° C. and caused to react at this temperature for 15 minutes. Extraction with ethyl acetate is carried out, and the ethyl acetate layer is washed with a saturated saline solution and thereafter dried over sodium sulfate. After filtration, the resultant is concentrated under a reduced pressure to yield a mixture containing the target compound.

$^1$H-NMR(CDCl$_3$); 1.37(s, 18H, t-Bux2), 1.43(s, 9H, t-Bu), 2.98(dd, J=8.4, 13.6, 1H, CH$_2$-α), 3.20(dd, J=5.6, 14.0, 1H, CH$_2$-β), 4.51(m, 1H, CH), 5.04(d, J=9.2, 1H, NH), 7.10(d, J=8.0, 1H, NH), 7.39(dd, J=1.6, 8.0, 1H, Ar), 7.97(d, J=1.6, 1H, Ar).

UPLC analysis conditions; column: BEH C18 column (130 A 1.7 μm 2.1 mm×150 mm), flow rate: 0.4 mL/min, detection: 254 nm, developing solvent: 0.1% acetic acid water:acetonitrile=30:70, detection period: 3.8 min.

Production of (2-(3-tert-butoxy-2-(benzyloxycarbonylamino)-3-oxopropyl)-5-bromophenyl)(4-methylphenyl)iodonium bromide The compound (2-(3-tert-butoxy-2-(benzyloxycarbonylamino)-3-oxopropyl)-5-bromophenyl)(4-methylphenyl) iodonium tosylate (58.9 mg, 0.07 mmol) is dissolved into ethyl acetate-water mixture liquid (1:1, 2 mL), and potassium bromide (39.4 mg, 0.33 mmol) is added thereto. The resultant is caused to react at room temperature for 5 hours. Extraction with ethyl acetate is carried out, and the ethyl acetate layer is dried over sodium sulfate. After filtration, the resultant is concentrated under a reduced pressure to yield the target compound (52.3 mg, 99%).

$^1$H-NMR(CDCl$_3$); 1.38-1.54(m, 27H, t-Bu), 2.37(s, 3H, Ar—CH$_3$), 3.40(dd, J=8.4, 14.4, 1H, CH$_2$-α), 3.61(dd, J=7.2, 14.4, 1H, CH$_2$-β), 5.06(t, J=7.6, 1H, CH), 7.19(d, J=8.0, 2H, Ar), 7.26(d, J=8.0, 1H, Ar), 7.52(dd, J=1.6, 8.0, 1H, Ar), 7.85(d, J=1.6, 1H, Ar), 7.95(d, J=8.4, 2H, Ar).

Production of tert-butyl 2-(bis(tert-butoxycarbonyl)amino)-3-(4-bromo-2-(4,4,5,5-tetramethyl-1,3,2-dioxaborolane-2-yl)phenyl)propanoate PdCl$_2$(dppf) (98 mg, 0.120 mmol), Bis(pinacolato)diboran (638 mg, 2.51 mmol), and potassium acetate were dissolved into DMSO (7.5 mL) in an Ar atmosphere, and the resultant was kept being stirred at room temperature. After a DMSO solution (4.5 mL) of the compound tert-butyl 2-(bis(tert-butoxycarbonyl)amino)-3-(4-bromo-2-iodophenyl)propanoate (1.50 g, 2.40 mmol) was added thereinto, the resultant was stirred at 80° C. for 24 hours. The reaction solution was diluted with ethyl acetate (70 mL) and subjected to Celite filtration. Thereafter, the resultant was washed with water and a saline solution, and the organic layer was dried over MgSO$_4$. The organic layer was filtrated, and the organic solvent was concentrated and then purified through column chromatography (hexane:ethyl acetate=9:1) to yield the target compound as a colorless oily substance (705 mg, 47%).

$^1$H-NMR(CDCl$_3$); 1.35-1.48(m, 39H, pinacol-CH$_3$×4, t-Bu), 3.08(dd, J=11.2, 13.6, 1H, CH$_2$-α), 3.89(dd, J=4.4, 14.0, 1H, CH$_2$-β), 5.17(dd, J=4.0, 11.2, 1H, CH), 6.91(d, J=8.0, 1H, Ar), 7.41(dd, J=2.0, 8.0, 1H, Ar), 7.89(d, J=2.0, 1H, Ar).

Production of tert-butyl 2-(bis(tert-butoxycarbonyl) amino)-3-(2-fluoro-4-bromophenyl)propanoate Tetrakis(pyridine)copper triflate (3.6 mg, 0.0053 mmol) was added to the compound obtained in the previous step (37.6 mg, 0.060 mmol). Further, potassium fluoride (3.8 mg, 0.066 mmol) and a DMF solution (4 mL) of 4,7,13,16,21, 24-hexaoxa-1,10-diazabicyclo[8.8.8]hexacosane (24.8 mg, 0.066 mmol) were added. The resultant was caused to react at 130° C. for 20 minutes. Thereafter, the resultant was filtrated and then concentrated under a reduced pressure to yield a mixture containing the target compound.

$^1$H-NMR(CDCl$_3$); 1.37(s, 18H, t-Bux2), 1.43(s, 9H, t-Bu), 2.98(dd, J=8.4, 13.6, 1H, CH$_2$-α), 3.20(dd, J=5.6, 14.0, 1H, CH$_2$-β), 4.51(m, 1H, CH), 5.04(d, J=9.2, 1H, NH), 7.10(d, J=8.0, 1H, NH), 7.39(dd, J=1.6, 8.0, 1H, Ar), 7.97(d, J=1.6, 1H, Ar).

Example 5

Production of 2-fluoro-4-iodobenzyl bromide

The target compound 2-fluoro-4-iodobenzyl bromide is obtained by employing the same method as that of Step S-2.

$^1$H-NMR(CDCl$_3$); 4.45(s, 2H, CH$_2$), 7.12(t, J=8.0, 1H, Ar), 7.45(d, J=8.4, 1H, Ar), 7.48(d, J=8.4, 1H, Ar).

Production of ethyl 3-(2-fluoro-4-iodophenyl)-2-(diphenylmethyleneamino)propanoate The target compound 703 is obtained by causing the compound obtained in the previous step to react with ethyl N-(diphenylmethylene)glycinate in place of benzyl N-(diphenylmethylene)glycinate by employing the same method as that of Step S-3. Here, the obtained compound is subjected to the next step without being purified.

Production of ethyl 2-amino-3-(2-fluoro-4-iodophenyl)propanoate

The target compound 704 was obtained by employing the same method as that of Step S-4.

$^1$H-NMR(CDCl$_3$); 1.24(t, J=7.2, 3H, CH$_2$CH$_3$), 2.86(dd, J=8.0, 13.6, 1H, CH$_2$-α), 3.04(dd, J=5.9, 14.0, 1H, CH$_2$-β), 3.71(dd, J=6.0, 7.6, 1H, CH), 4.16(q, J=7.2, 2H, CH$_2$CH$_3$), 6.95(t, J=8.0, 1H, Ar), 7.40(d, J=7.6, 1H, Ar), 7.42(d, J=7.6, 1H, Ar).

Production of ethyl 3-(2-fluoro-4-iodophenyl)-2-(benzyloxycarbonylamino)propanoate The target compound 705 was obtained by employing the same method as that of Step S-5.

$^1$H-NMR(CDCl$_3$); 1.24(t, J=7.3, 3H, CH$_2$CH$_3$), 3.06(dd, J=6.8, 13.6, 1H, CH$_2$-α), 3.16(dd, J=4.8, 14.0, 1H, CH$_2$-β), 4.17(q, J=7.2, 2H, CH$_2$CH$_3$), 4.61(m, 1H, CH), 5.08(m, 2H, CH$_2$Ar), 5.29(d, J=8.0, 1H, NH), 6.84(t, J=7.6, 1H, Ar), 7.31-7.38(m, 7H, Ar).

Furthermore, the compound obtained in the previous step can be used to prepare a pinacol boronated compound in the same manner as in Example 1 or 3.

Reference Example 1

De-Protection of Pinacol Boronated Compound Labeled with Fluorine

The pinacol boronated compounds obtained in Examples 1 to 4 can be each de-protected to prepare a target fluorinated BPA. Specifically, first, Boc and t-Bu are de-protected by 4N HCl AcOEt.

Next, when elution is made by a reversed-layer column using a 0.1% acetic acid-acetonitrile solvent, pinacol also is removed, whereby the target fluorinated BPA is obtained.

What is claimed is:

1. A method for producing a compound represented by the following formula:

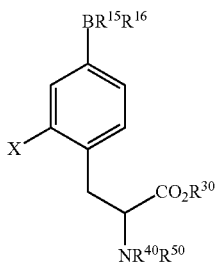

[Formula 2]

wherein X represents F or $^{18}$F; R$^{30}$ represents hydrogen, methyl group, an ethyl group, an n-propyl group, an iso-propyl group, an n-butyl group, an iso-butyl group, a sec-butyl group, a tert-butyl group, an n-pentyl group, or an aromatic group; R$^{40}$ and R$^{50}$ independently represent hydrogen, a benzyloxycarbonyl group, an acetyl group, a trifluoroethylcarboxy group, a tert-butyloxycarbonyl group, a fluorenylmethyloxycarbonyl group, a trichloroethoxycarbonyl group, a trifluoroacetyl group, an allyloxycarbonyl group, a benzyl group, a propargyloxycarbonyl group, a benzoyl group, a phthaloyl group, a toluenesulfonyl group, or a nitrobenzenesulfonyl group; and R$^{15}$ and R$^{16}$ are combined together with the boron atom to form a ring serving as a protecting group for the boron atom, wherein the group that forms the ring is selected from the group consisting of pinacol, 2,2-dimethyl-1,3-propanediol, N-methyldiethanolamine, 1,8-diaminonaphthalene, N-methyliminodiacetic acid, 1,1,1-trishydroxymethylethane, and catechol, comprising:

reacting a compound represented by the following formula:

[Formula 3]

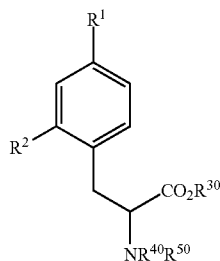

wherein $R^1$ represents a bromo group, an iodo group, a chloro group, a nitro group, or an amino group; $R^2$ represents a bromo group, an iodo group, a chloro group, a nitro group, an amino group, $OSO_2R^9$, $NR^{10}R^{11}$, substituted or unsubstituted phenyl iodo, a substituted or unsubstituted heterocyclic iodo group, or boric acid or a boric ester; $R^9$ represents an alkyl group having 1 to 7 carbon atoms, a halogen-substituted alkyl group having 1 to 7 carbon atoms, or an optionally substituted phenyl group; $R^{10}$ and $R^{11}$ are the same or different, each representing an alkyl group having 1 to 7 carbon atoms, a halogen-substituted alkyl group having 1 to 7 carbon atoms, or an optionally substituted phenyl group, or else $R^{10}$ and $R^{11}$ are combined together with N to form a 3- to 7-membered cyclic structure; and $R^{30}$, $R^{40}$, and $R^{50}$ have the same meaning as described above, wherein said reacting comprises reacting said compound in presence of a fluorinating agent in a solvent to obtain fluorinated compound and then radiating the resulting fluorinated compound in the presence of boronation reagent, a catalyst, and a ligand.

2. The method of claim 1, wherein the catalyst is a palladium catalyst.

3. The method of claim 2, wherein the palladium catalyst is selected from the group consisting of a palladium chloride cinnamyl complex, palladium acetate, and trisdibenzylideneacetonedipalladium.

4. The method of claim 1, wherein the radiating comprises microwave radiation.

5. The method of claim 4, wherein the microwave radiation is conducted from room temperature to 200° C.

6. The method of claim 4, wherein the reaction period is from 1 minute to 60 minutes.

7. The method of claim 1, wherein the ligand is a phosphorus-based ligand.

8. The method of claim 7, wherein the phosphorus-based ligand is selected from the group consisting of tricyclohexylphosphine, 2-dicyclohexylphosphino-2,4,6-triisopropylbiphenyl, 2-dicyclohexylphosphino-2,-(N,N)-dimethylaminobiphenyl, 3,5-dimethoxy-2-dicyclohexylphosphino-2,4,6-triisopropylbiphenyl, and 3,5-dimethoxy-2-ditert-butylphosphino-2,4,6-triisopropylbiphenyl.

9. The method of claim 1, wherein the reacting is conducted in the presence of a base.

10. The method of claim 9, wherein the base is selected from the group consisting of lithium hydroxide, sodium hydroxide, potassium hydroxide, sodium carbonate, potassium carbonate, and trimethylamine.

11. The method of claim 1, wherein the reacting is conducted in a solvent selected from the group consisting of toluene, dioxane, and DMDO.

12. The method of claim 1, wherein $R^{30}$ represents an aromatic group selected from the group consisting of benzyl, p-methoxybenzyl, and p-nitrobenzyl.

* * * * *